US008795703B2

(12) United States Patent
Swanick et al.

(10) Patent No.: US 8,795,703 B2
(45) Date of Patent: *Aug. 5, 2014

(54) STAND-ALONE FILM AND METHODS FOR MAKING THE SAME

(75) Inventors: Thomas M. Swanick, Hillsborough, NH (US); Joseph Ferraro, Londonderry, NH (US); Paul Martakos, Pelham, NH (US); Lisa Rogers, Londonderry, NH (US); Theodore Karwoski, Hollis, NH (US); Steve A. Herweck, Nashua, NH (US); Keith Faucher, Nashua, NH (US); Philip McNamara, Concord, NH (US)

(73) Assignee: Atrium Medical Corporation, Hudson, NH (US)

( * ) Notice: Subject to any disclaimer, the term of this patent is extended or adjusted under 35 U.S.C. 154(b) by 2040 days.

This patent is subject to a terminal disclaimer.

(21) Appl. No.: 11/237,264

(22) Filed: Sep. 28, 2005

(65) Prior Publication Data
US 2006/0067983 A1 Mar. 30, 2006

Related U.S. Application Data

(60) Provisional application No. 60/613,808, filed on Sep. 28, 2004.

(51) Int. Cl.
A61F 2/00 (2006.01)
A61K 9/14 (2006.01)
A61K 35/60 (2006.01)

(52) U.S. Cl.
USPC ............ 424/423; 424/426; 424/484; 424/523

(58) Field of Classification Search
None
See application file for complete search history.

(56) References Cited

U.S. PATENT DOCUMENTS

| | | |
|---|---|---|
| 2,368,306 A | 1/1945 | Kiefer et al. |
| 2,986,540 A | 5/1961 | Posnansky |
| 3,464,413 A | 9/1969 | Goldfarb et al. |
| 3,556,294 A | 1/1971 | Walck et al. |
| 3,567,820 A | 3/1971 | Sperti |
| 3,803,109 A | 4/1974 | Nemoto et al. |
| 3,967,728 A | 7/1976 | Gordon et al. |
| 4,308,120 A | 12/1981 | Pennewiss et al. |
| 4,323,547 A | 4/1982 | Knust et al. |
| 4,557,925 A | 12/1985 | Lindahl et al. |
| 4,664,114 A | 5/1987 | Ghodstain |
| 4,813,210 A | 3/1989 | Masuda et al. |
| 4,814,329 A | 3/1989 | Harsanyi et al. |
| 4,847,301 A | 7/1989 | Murray |
| 4,880,455 A | 11/1989 | Blank |
| 4,883,667 A | 11/1989 | Eckenhoff |
| 4,886,787 A | 12/1989 | De Belder et al. |
| 4,894,231 A | 1/1990 | Moreau et al. |
| 4,895,724 A | 1/1990 | Cardinal et al. |
| 4,911,707 A | 3/1990 | Heiber et al. |
| 4,938,763 A * | 7/1990 | Dunn et al. ................ 604/891.1 |
| 4,941,308 A | 7/1990 | Grabenkort et al. |
| 4,952,419 A | 8/1990 | Ferguson et al. |
| 4,968,302 A | 11/1990 | Schluter et al. |
| 5,017,229 A | 5/1991 | Burns et al. |
| 5,132,115 A | 7/1992 | Wolter et al. |
| 5,147,374 A | 9/1992 | Fernandez |
| 5,151,272 A | 9/1992 | Engstrom et al. |
| 5,171,148 A | 12/1992 | Wasserman et al. |
| 5,176,956 A | 1/1993 | Jevne et al. |
| 5,179,174 A | 1/1993 | Elton |
| 5,254,105 A | 10/1993 | Haaga |
| 5,356,432 A | 10/1994 | Rutkow et al. |
| 5,368,602 A | 11/1994 | de la Torre |
| 5,371,109 A | 12/1994 | Engstrom et al. |
| 5,380,328 A | 1/1995 | Morgan |
| 5,387,658 A | 2/1995 | Schroder et al. |
| 5,403,283 A | 4/1995 | Luther |
| 5,447,940 A | 9/1995 | Harvey et al. |
| 5,464,650 A | 11/1995 | Berg et al. |
| 5,480,653 A | 1/1996 | Aguadish et al. |
| 5,509,899 A | 4/1996 | Fan et al. |
| 5,579,149 A | 11/1996 | Moret et al. |
| 5,580,923 A | 12/1996 | Yeung et al. |
| 5,591,230 A | 1/1997 | Horn et al. |
| 5,593,441 A | 1/1997 | Lichtenstein et al. |
| 5,612,074 A | 3/1997 | Leach |
| 5,614,284 A | 3/1997 | Kranzler et al. |
| 5,627,077 A | 5/1997 | Dyllick-Brenzinger et al. |

(Continued)

FOREIGN PATENT DOCUMENTS

| | | |
|---|---|---|
| EP | 0471566 | 2/1992 |
| EP | 0610731 | 8/1994 |

(Continued)

OTHER PUBLICATIONS

International Search Report for Application No. PCT/US05/34682, dated Jul. 20, 2006.
European Office Action for Application No. 07838216.5, dated Feb. 11, 2010.
Redman, L.V. et al., "The drying rate of raw paint oils—a comparison," The Journal of Industrial and Engineering Chemistry, vol. 5: 630-636 (1913).
Guler et al. (Some empirical equations for oxopolymerization of linseed oil. Progress in Organic Coatings 2004, vol. 51, 365-371).
"Cure" in Academic Press Dictionary of Science and Technology (1992).
Autosuture, "Parietex™ Composite OS SERIES MESH," retrieved online at http://www.autosuture.com/AutoSuture/pagebuilder.aspx?topicID=135734&breadcrumbs=135601:0 (2007).

(Continued)

Primary Examiner — Michael G Hartley
Assistant Examiner — Nabila Ebrahim

(57) ABSTRACT

A stand-alone film is derived at least in part from fatty acids. The stand-alone film can have anti-adhesive, anti-inflammatory, non-inflammatory, and wound healing properties, and can additionally include one or more therapeutic agents incorporated therein. Corresponding methods of making the stand-alone film include molding, casting, or otherwise applying a liquid or gel to a substrate, and curing or otherwise treating to form the stand-alone film. The resulting stand-alone film is bioabsorbable.

33 Claims, 7 Drawing Sheets

(56) References Cited

U.S. PATENT DOCUMENTS

| | | |
|---|---|---|
| 5,637,113 A | 6/1997 | Tartaglia et al. |
| 5,665,115 A | 9/1997 | Cragg |
| 5,695,525 A | 12/1997 | Mulhauser et al. |
| 5,700,286 A | 12/1997 | Tartaglia et al. |
| 5,736,152 A * | 4/1998 | Dunn ............................ 424/426 |
| 5,753,259 A | 5/1998 | Engstrom et al. |
| 5,760,081 A | 6/1998 | Leaf et al. |
| 5,766,246 A | 6/1998 | Mulhauser et al. |
| 5,766,710 A | 6/1998 | Turnlund et al. |
| 5,789,465 A | 8/1998 | Harvey et al. |
| 5,817,343 A | 10/1998 | Burke |
| 5,824,082 A | 10/1998 | Brown |
| 5,837,313 A | 11/1998 | Ding et al. |
| 5,843,919 A | 12/1998 | Burger |
| 5,874,470 A | 2/1999 | Nehne et al. |
| 5,879,359 A | 3/1999 | Dorigatti et al. |
| 5,898,040 A | 4/1999 | Shalaby et al. |
| 5,906,831 A | 5/1999 | Larsson et al. |
| 5,931,165 A | 8/1999 | Reich et al. |
| 5,955,502 A | 9/1999 | Hansen et al. |
| 5,986,043 A | 11/1999 | Hubbell et al. |
| 6,005,004 A | 12/1999 | Katz et al. |
| 6,010,766 A | 1/2000 | Braun et al. |
| 6,010,776 A | 1/2000 | Exsted et al. |
| 6,015,844 A | 1/2000 | Harvey et al. |
| 6,028,164 A | 2/2000 | Loomis |
| 6,040,330 A | 3/2000 | Hausheer et al. |
| 6,056,970 A | 5/2000 | Greenawalt et al. |
| 6,077,698 A | 6/2000 | Swan et al. |
| 6,083,950 A | 7/2000 | Anand et al. |
| 6,090,809 A | 7/2000 | Anand et al. |
| 6,093,792 A | 7/2000 | Gross et al. |
| 6,117,911 A | 9/2000 | Grainger et al. |
| 6,120,789 A * | 9/2000 | Dunn ............................ 424/426 |
| 6,132,765 A | 10/2000 | DiCosmo et al. |
| 6,146,358 A | 11/2000 | Rowe |
| 6,152,944 A | 11/2000 | Holman et al. |
| 6,176,863 B1 | 1/2001 | Kugel et al. |
| 6,193,746 B1 | 2/2001 | Strecker |
| 6,197,357 B1 | 3/2001 | Lawton et al. |
| 6,203,551 B1 | 3/2001 | Wu |
| 6,206,916 B1 | 3/2001 | Furst |
| 6,211,315 B1 | 4/2001 | Larock et al. |
| 6,228,383 B1 | 5/2001 | Hansen et al. |
| 6,229,032 B1 | 5/2001 | Jacobs et al. |
| 6,245,811 B1 | 6/2001 | Harrobin et al. |
| 6,254,634 B1 | 7/2001 | Anderson et al. |
| 6,262,109 B1 | 7/2001 | Clark et al. |
| 6,273,913 B1 | 8/2001 | Wright et al. |
| 6,284,268 B1 | 9/2001 | Mishra et al. |
| 6,299,604 B1 | 10/2001 | Ragheb et al. |
| 6,326,360 B1 | 12/2001 | Kanazawa et al. |
| 6,331,568 B1 | 12/2001 | Horrobin |
| 6,342,254 B1 | 1/2002 | Soudant et al. |
| 6,346,110 B2 | 2/2002 | Wu |
| 6,358,556 B1 | 3/2002 | Ding et al. |
| 6,364,893 B1 | 4/2002 | Sahatjian et al. |
| 6,368,658 B1 | 4/2002 | Schwarz et al. |
| 6,369,039 B1 | 4/2002 | Palasis et al. |
| 6,387,379 B1 | 5/2002 | Goldberg et al. |
| 6,410,587 B1 | 6/2002 | Grainger et al. |
| 6,444,318 B1 | 9/2002 | Guire et al. |
| 6,451,373 B1 | 9/2002 | Hossainy et al. |
| 6,465,525 B1 | 10/2002 | Guire et al. |
| 6,471,980 B2 | 10/2002 | Sirhan et al. |
| 6,479,683 B1 | 11/2002 | Abney et al. |
| 6,491,938 B2 | 12/2002 | Kunz |
| 6,500,453 B2 | 12/2002 | Brey et al. |
| 6,503,556 B2 | 1/2003 | Harish et al. |
| 6,525,145 B2 | 2/2003 | Gevaert et al. |
| 6,527,801 B1 | 3/2003 | Dutta |
| 6,534,693 B2 | 3/2003 | Fischell et al. |
| 6,548,081 B2 | 4/2003 | Sadozai et al. |
| 6,565,659 B1 | 5/2003 | Pacetti et al. |
| 6,569,441 B2 | 5/2003 | Kunz et al. |
| 6,599,323 B2 | 7/2003 | Melican et al. |
| 6,610,035 B2 | 8/2003 | Yang et al. |
| 6,610,068 B1 | 8/2003 | Yang et al. |
| 6,630,151 B1 | 10/2003 | Tarletsky et al. |
| 6,630,167 B2 | 10/2003 | Zhang |
| 6,632,822 B1 | 10/2003 | Rickards et al. |
| 6,641,611 B2 | 11/2003 | Jayaraman |
| 6,645,547 B1 | 11/2003 | Shekalim |
| 6,663,880 B1 | 12/2003 | Roorda et al. |
| 6,669,735 B1 | 12/2003 | Pelissier |
| 6,670,355 B2 | 12/2003 | Azrolan et al. |
| 6,677,342 B2 | 1/2004 | Wolff et al. |
| 6,677,386 B1 | 1/2004 | Giezen et al. |
| 6,685,956 B2 | 2/2004 | Chu et al. |
| 6,730,064 B2 | 5/2004 | Ragheb et al. |
| 6,753,071 B1 | 6/2004 | Pacetti |
| 6,761,903 B2 | 7/2004 | Chen et al. |
| 6,764,509 B2 | 7/2004 | Chinn et al. |
| 6,776,796 B2 | 8/2004 | Falotico et al. |
| 6,794,485 B2 | 9/2004 | Shalaby et al. |
| 6,833,004 B2 | 12/2004 | Ishii et al. |
| 6,852,330 B2 | 2/2005 | Bowman et al. |
| 6,875,230 B1 | 4/2005 | Morita et al. |
| 6,884,428 B2 | 4/2005 | Binette et al. |
| 6,887,270 B2 | 5/2005 | Miller et al. |
| 6,899,729 B1 | 5/2005 | Cox et al. |
| 6,918,927 B2 | 7/2005 | Bates et al. |
| 6,996,952 B2 | 2/2006 | Gupta et al. |
| 7,070,858 B2 | 7/2006 | Shalaby et al. |
| 7,101,381 B2 | 9/2006 | Ford et al. |
| 7,152,611 B2 | 12/2006 | Brown et al. |
| 7,323,189 B2 | 1/2008 | Pathak |
| 7,415,811 B2 | 8/2008 | Gottlieb et al. |
| 8,124,127 B2 | 2/2012 | Faucher et al. |
| 8,263,102 B2 | 9/2012 | Labrecque et al. |
| 8,312,836 B2 | 11/2012 | Corbeil et al. |
| 8,367,099 B2 | 2/2013 | Herweck et al. |
| 8,501,229 B2 | 8/2013 | Faucher et al. |
| 8,722,077 B2 | 5/2014 | Labrecque et al. |
| 2001/0025034 A1 | 9/2001 | Arbiser |
| 2001/0025196 A1 | 9/2001 | Chinn et al. |
| 2001/0051595 A1 | 12/2001 | Lyons et al. |
| 2002/0002154 A1 | 1/2002 | Guivarc'h et al. |
| 2002/0007209 A1 | 1/2002 | Scheerder et al. |
| 2002/0012741 A1 | 1/2002 | Heinz et al. |
| 2002/0026899 A1 | 3/2002 | McLaughlin et al. |
| 2002/0026900 A1 | 3/2002 | Huang et al. |
| 2002/0032414 A1 | 3/2002 | Ragheb et al. |
| 2002/0055701 A1 | 5/2002 | Fischell et al. |
| 2002/0098278 A1 | 7/2002 | Bates et al. |
| 2002/0116045 A1 | 8/2002 | Eidenschink |
| 2002/0120333 A1 | 8/2002 | Keogh et al. |
| 2002/0122877 A1 | 9/2002 | Harish et al. |
| 2002/0142089 A1 | 10/2002 | Koike et al. |
| 2002/0193829 A1 | 12/2002 | Kennedy et al. |
| 2003/0003125 A1 | 1/2003 | Nathan et al. |
| 2003/0003221 A1 | 1/2003 | Zhong et al. |
| 2003/0004564 A1 | 1/2003 | Elkins et al. |
| 2003/0055403 A1 | 3/2003 | Nestenborg et al. |
| 2003/0065292 A1 | 4/2003 | Darouiche et al. |
| 2003/0065345 A1 * | 4/2003 | Weadock ...................... 606/153 |
| 2003/0069632 A1 | 4/2003 | De Scheerder et al. |
| 2003/0072784 A1 | 4/2003 | Williams |
| 2003/0077272 A1 | 4/2003 | Pathak |
| 2003/0077310 A1 | 4/2003 | Pathak et al. |
| 2003/0077452 A1 | 4/2003 | Guire et al. |
| 2003/0083740 A1 | 5/2003 | Pathak |
| 2003/0086958 A1 | 5/2003 | Arnold et al. |
| 2003/0094728 A1 | 5/2003 | Tayebi |
| 2003/0108588 A1 | 6/2003 | Chen et al. |
| 2003/0130206 A1 | 7/2003 | Koziak et al. |
| 2003/0152609 A1 | 8/2003 | Fischell et al. |
| 2003/0175408 A1 | 9/2003 | Timm et al. |
| 2003/0176915 A1 | 9/2003 | Wright et al. |
| 2003/0181975 A1 | 9/2003 | Ishii et al. |
| 2003/0191179 A1 | 10/2003 | Joshi-Hangal et al. |
| 2003/0204168 A1 | 10/2003 | Bosma et al. |
| 2003/0204618 A1 | 10/2003 | Foster et al. |
| 2003/0207019 A1 | 11/2003 | Shekalim et al. |

(56) References Cited

U.S. PATENT DOCUMENTS

| | | |
|---|---|---|
| 2003/0211230 A1 | 11/2003 | Pacetti et al. |
| 2003/0220297 A1 | 11/2003 | Berstein et al. |
| 2004/0006296 A1 | 1/2004 | Fischell et al. |
| 2004/0014810 A1 | 1/2004 | Horrobin |
| 2004/0018228 A1 | 1/2004 | Fischell et al. |
| 2004/0039441 A1 | 2/2004 | Rowland et al. |
| 2004/0060260 A1 | 4/2004 | Gottlieb et al. |
| 2004/0071756 A1 | 4/2004 | Fischell et al. |
| 2004/0072849 A1 | 4/2004 | Schreiber et al. |
| 2004/0073284 A1 | 4/2004 | Bates et al. |
| 2004/0131755 A1 | 7/2004 | Zhong et al. |
| 2004/0133275 A1 | 7/2004 | Mansmann |
| 2004/0137066 A1 | 7/2004 | Jayaraman |
| 2004/0137179 A1 | 7/2004 | Shojiro et al. |
| 2004/0142094 A1 | 7/2004 | Narayanan |
| 2004/0146546 A1 | 7/2004 | Gravett et al. |
| 2004/0156879 A1 | 8/2004 | Muratoglu et al. |
| 2004/0161464 A1 | 8/2004 | Domb |
| 2004/0167572 A1 | 8/2004 | Roth et al. |
| 2004/0170685 A1 | 9/2004 | Carpenter et al. |
| 2004/0192643 A1 | 9/2004 | Pressato et al. |
| 2004/0215219 A1 | 10/2004 | Eldridge et al. |
| 2004/0224003 A1 | 11/2004 | Schultz |
| 2004/0230176 A1 | 11/2004 | Shanahan et al. |
| 2004/0234574 A9 | 11/2004 | Sawhney et al. |
| 2004/0241211 A9 | 12/2004 | Fischell |
| 2004/0256264 A1 | 12/2004 | Israelsson et al. |
| 2005/0010078 A1 | 1/2005 | Jamiolkowski et al. |
| 2005/0084514 A1 | 4/2005 | Shebuski et al. |
| 2005/0095267 A1 | 5/2005 | Campbell et al. |
| 2005/0100655 A1 | 5/2005 | Zhong et al. |
| 2005/0106209 A1 | 5/2005 | Ameri et al. |
| 2005/0112170 A1 | 5/2005 | Hossainy et al. |
| 2005/0113849 A1 | 5/2005 | Popadiuk et al. |
| 2005/0129787 A1 | 6/2005 | Murad |
| 2005/0158361 A1 | 7/2005 | Dhondt et al. |
| 2005/0159809 A1 | 7/2005 | Hezi-Yamit et al. |
| 2005/0165476 A1 | 7/2005 | Furst et al. |
| 2005/0165477 A1 | 7/2005 | Anduiza et al. |
| 2005/0182485 A1 | 8/2005 | Falotico et al. |
| 2005/0187376 A1 | 8/2005 | Pacetti |
| 2005/0203635 A1 | 9/2005 | Hunter et al. |
| 2005/0203636 A1 | 9/2005 | McFetridge |
| 2005/0223679 A1 | 10/2005 | Gottlieb et al. |
| 2005/0232971 A1 | 10/2005 | Hossainy et al. |
| 2005/0249775 A1 | 11/2005 | Falotico et al. |
| 2005/0283229 A1 | 12/2005 | Dugan et al. |
| 2006/0008501 A1 | 1/2006 | Dhont et al. |
| 2006/0036311 A1 | 2/2006 | Nakayama et al. |
| 2006/0058881 A1 | 3/2006 | Trieu |
| 2006/0067974 A1 | 3/2006 | Labrecque |
| 2006/0067975 A1 | 3/2006 | Labrecque et al. |
| 2006/0067976 A1 | 3/2006 | Ferraro et al. |
| 2006/0067977 A1 | 3/2006 | Labrecque et al. |
| 2006/0067983 A1 | 3/2006 | Swanick et al. |
| 2006/0068674 A1 | 3/2006 | Dixit et al. |
| 2006/0078586 A1 | 4/2006 | Ferraro |
| 2006/0083768 A1 | 4/2006 | Labrecque et al. |
| 2006/0088596 A1 | 4/2006 | Labrecque |
| 2006/0093643 A1 | 5/2006 | Stenzel |
| 2006/0110457 A1 | 5/2006 | Labrecque et al. |
| 2006/0121081 A1 | 6/2006 | Labrecque et al. |
| 2006/0124056 A1 | 6/2006 | Behnisch et al. |
| 2006/0134209 A1 | 6/2006 | Labhasetwar et al. |
| 2006/0158361 A1 | 7/2006 | Chou |
| 2006/0204738 A1 | 9/2006 | Dubrow et al. |
| 2006/0210701 A1 | 9/2006 | Chappa et al. |
| 2006/0240069 A1 | 10/2006 | Utas et al. |
| 2006/0246105 A1 | 11/2006 | Molz et al. |
| 2007/0015893 A1 | 1/2007 | Hakuta et al. |
| 2007/0071798 A1 | 3/2007 | Herweck et al. |
| 2007/0084144 A1 | 4/2007 | Labrecque et al. |
| 2007/0093894 A1 | 4/2007 | Darouiche |
| 2007/0141112 A1 | 6/2007 | Falotico et al. |
| 2007/0202149 A1 | 8/2007 | Faucher et al. |
| 2007/0212411 A1 | 9/2007 | Fawzy et al. |
| 2007/0264460 A1 | 11/2007 | Del Tredici |
| 2007/0275074 A1 | 11/2007 | Holm et al. |
| 2007/0280986 A1 | 12/2007 | Gil et al. |
| 2007/0286891 A1 | 12/2007 | Kettlewell et al. |
| 2007/0299538 A1 | 12/2007 | Roeber |
| 2008/0038307 A1 | 2/2008 | Hoffmann |
| 2008/0044481 A1 | 2/2008 | Harel |
| 2008/0045557 A1 | 2/2008 | Grainger et al. |
| 2008/0086216 A1 | 4/2008 | Wilson et al. |
| 2008/0109017 A1 | 5/2008 | Herweck et al. |
| 2008/0113001 A1 | 5/2008 | Herweck et al. |
| 2008/0118550 A1 | 5/2008 | Martakos et al. |
| 2008/0206305 A1 | 8/2008 | Herweck et al. |
| 2008/0279929 A1 | 11/2008 | Devane et al. |
| 2008/0286440 A1 | 11/2008 | Scheer |
| 2008/0289300 A1 | 11/2008 | Gottlieb et al. |
| 2009/0011116 A1 | 1/2009 | Herweck et al. |
| 2009/0047414 A1 | 2/2009 | Corbeil et al. |
| 2009/0181937 A1 | 7/2009 | Faucher |
| 2009/0208552 A1 | 8/2009 | Faucher |
| 2010/0183697 A1 | 7/2010 | Swanick et al. |
| 2010/0209473 A1 | 8/2010 | Dhont et al. |
| 2010/0233232 A1 | 9/2010 | Swanick et al. |
| 2011/0274823 A1 | 11/2011 | Labrecque et al. |
| 2012/0016038 A1 | 1/2012 | Faucher et al. |
| 2012/0213839 A1 | 8/2012 | Faucher et al. |

FOREIGN PATENT DOCUMENTS

| | | |
|---|---|---|
| EP | 0623354 | 11/1994 |
| EP | 0730864 | 9/1996 |
| EP | 0790822 | 8/1997 |
| EP | 0873133 | 10/1998 |
| EP | 0917561 | 5/1999 |
| EP | 1140243 | 10/2001 |
| EP | 1181943 | 2/2002 |
| EP | 1270024 | 1/2003 |
| EP | 1273314 | 1/2003 |
| EP | 1364628 | 11/2003 |
| EP | 1520795 | 4/2005 |
| EP | 1557183 | 7/2005 |
| EP | 2083875 | 8/2009 |
| EP | 1402906 | 6/2011 |
| KR | 20080025986 | 3/2008 |
| WO | WO 86/00912 | 7/1984 |
| WO | WO 90/01969 | 3/1990 |
| WO | WO 95/26715 | 10/1995 |
| WO | WO 97/02042 | 1/1997 |
| WO | WO 97/09367 | 3/1997 |
| WO | WO 97/13528 | 4/1997 |
| WO | WO 98/30206 | 7/1998 |
| WO | WO 98/54275 | 12/1998 |
| WO | WO 99/25336 | 5/1999 |
| WO | WO 00/40278 | 7/2000 |
| WO | WO 0040278 | 7/2000 |
| WO | WO 00/62830 | 10/2000 |
| WO | WO 0062830 | 10/2000 |
| WO | WO 01/24866 | 4/2001 |
| WO | WO 01/26585 | 4/2001 |
| WO | WO 01/37808 | 5/2001 |
| WO | WO 01/60586 | 8/2001 |
| WO | WO 01/66036 | 9/2001 |
| WO | WO 01/76649 | 10/2001 |
| WO | WO 02/49535 | 6/2002 |
| WO | WO 02/100455 | 12/2002 |
| WO | WO 02100455 | 12/2002 |
| WO | WO 03/000308 | 1/2003 |
| WO | WO 03000308 | 1/2003 |
| WO | WO 03/015748 | 2/2003 |
| WO | WO 03/028622 | 4/2003 |
| WO | WO 03/037397 | 5/2003 |
| WO | WO 03/037398 | 5/2003 |
| WO | WO 03/039612 | 5/2003 |
| WO | WO 03/041756 | 5/2003 |
| WO | WO 03039612 A1 * | 5/2003 |
| WO | WO 03/070125 | 8/2003 |
| WO | WO 03/092741 | 11/2003 |
| WO | WO 03/092779 | 11/2003 |

(56) References Cited

FOREIGN PATENT DOCUMENTS

| WO | WO 2004/004598 | 1/2004 |
|---|---|---|
| WO | WO 2004/006976 | 1/2004 |
| WO | WO 2004/006978 | 1/2004 |
| WO | WO 2004/028583 | 4/2004 |
| WO | WO 2004/091684 | 10/2004 |
| WO | WO 2005/000165 | 1/2005 |
| WO | WO 2005/016400 | 2/2005 |
| WO | WO 2005/053767 | 6/2005 |
| WO | WO 2005/073091 | 8/2005 |
| WO | WO 2005/116118 | 12/2005 |
| WO | WO-2005/116118 A1 | 12/2005 |
| WO | WO 2006/024488 | 3/2006 |
| WO | WO 2006/036967 | 4/2006 |
| WO | WO 2006/102374 | 9/2006 |
| WO | WO 2007/047028 | 4/2007 |
| WO | WO-2007/047028 A1 | 4/2007 |
| WO | WO 2008/057328 | 5/2008 |
| WO | WO 2012/009707 | 1/2012 |

OTHER PUBLICATIONS

Binder et al., "Chromatographic Analysis of Seed Oils. Fatty Acid Composition of Castor Oil," The Journal of the American Oil Chemists' Society, vol. 39:513-517 (1962).
Camurus, "In our endeavors to create the unique, we start with the best. Your product."
CECW-EE, "Ch. 4: Coating Types and Characteristics," Engineering and Design—Painting: New Construction and Maintenance, pp. 4-1 to 4-24 (1995).
De Scheerder, Ivan K., et al. "Biocompatibility of polymer-coated oversized metallic stents implanted in normal porcine coronary arteries," Atherosclerosis, vol. 114:105-114.
Drummond, Calum J., et al., "Surfactant self-assembly objects as novel drug delivery vehicles," Current Opinion in Colliod & Interface Science, vol. 4:449-456 (2000).
Engstrom, Sven, "Drug Delivery from Cubic and Other Lipid-water Phases," Lipid Technology, vol. 2(2):42-45 (1990).
Guler, et al. "Some empirical equations for oxopolymerization of linseed oil," Progress in Organic Coatings, vol. 51:365-371 (2004).
Hwang, Chao-Wei, et al, "Physiological Transport Forces Govern Drug Distribution for Stent-Based Delivery," Circulation, vol. 104:600-605 (2001).
Mallegol, et al., "Drier Influence on the Curing of Linseed Oil," Progress in Organic Coatings 39:107-113 (2000).
Morse, Richard "Molecular Distillation of Polymerized Drying Oils," Industrial and Engineering Chemisry 33:1039-1043 (1941).
Oberhoff, Martin, et al, "Local and Systemic Delivery of Low Molecular Weight Heparin Following PTCA: Acute Results and 6-Month Follow-Up of the Initial Clinical Experience With the Porous Balloon (PILOT-Study)," Catheterization and Cardiovascular Diagnosis, vol. 44:267-274 (1998).
Salu, Koen J., et al, "Addition of cytochalasin D to a biocompatible oil stent coating inhibits intimal hyperplasia in a porcine coronary model," Coronary Artery Disease, vol. 14(8):545-555 (2003).
Scheller, Bruno, et al, "Addition of Paclitaxel to Contrast Media Prevents Restenosis After Coronary Stent Implantation," Journal of the American College of Cardiology, vol. 42(8):1415-1420 (2003).
Van der Giessen, Willem J., et al, "Marked Inflammatory Sequelae to Implantation of Biodegradable and Nonbiodegradable Polymers in Porcine Coronary Arteries," Circulation, vol. 94:1690-1697 (1996).
Wikipedia, "Sirolimus," pp. 1-13, available online at http://en.wikipedia.org/wiki/Sirolimus, date accessed May 11, 2011.
Crivello et al., "Epoxidized triglycerides as renewable monomers in photoinitiated cationic polymerization," Chem. Mater, 1992:692-699.
Encylopedia Britannica Online, "Surface Coating," available online at http://www.britannica.com/EBchecked/topic/575029/surface-coating>, date accessed Jun. 17, 2011.
Timir-Balizsy et al., "Chemical Principals of Textile Conservation," Oxford: Elsevier Science Ltd., 1998:117-119.

International Search Report for International Application PCT/US05/034601, dated Apr. 10, 2006.
International Search Report for International Application PCT/US05/034610, dated Mar. 16, 2006.
International Search Report for International Application PCT/US05/034614, dated Aug. 29, 2006.
International Search Report for International Application PCT/US05/034615, dated May 16, 2006.
International Search Report for International Application PCT/US05/034678, dated Aug. 28, 2006.
nternational Search Report for International Application PCT/US05/034681, dated Jul. 26, 2006.
International Search Report for International Application PCT/US05/034682, dated Jul. 20, 2006.
International Search Report for International Application PCT/US05/034836, dated Jul. 6, 2006.
International Search Report for International Application PCT/US06/037184, dated Feb. 22 2007.
International Preliminary Report on Patentability for International Application PCT/US06/040753, dated Oct. 3, 2008.
International Search Report for International Application PCT/US06/040753, dated Sep. 24, 2007.
International Search Report for International Application PCT/US07/019978, dated May 7, 2009.
International Search Report for Internat onal Applicat on PCT/US07/022860, dated Apr. 22, 2009.
International Search Report for International Application PCT/US07/022944, dated Apr. 8, 2009.
International Search Report for International Appl cation PCT/US08/000565, dated May 4, 2009.
International Preliminary Examination Report for International Application PCT/US08/071547, dated Aug. 26, 2010.
International Search Report for International Application PCT/US08/071547, dated Oct. 22, 2008.
International Preliminary Report on Patentability for International Application PCT/US08/071565, dated Aug. 27, 2009.
International Search Report for International Application PCT/US08/071565, dated Nov. 10, 2008.
International Search Report o nternational Application PCT/US08/085386, dated Feb. 4, 2009.
International Search Report for International Application PCT/US09/037364, dated Aug. 27, 2009.
International Search Report for International Application PCT/US10/026521, dated Jun. 23, 2010.
International Search Report for International Application PCT/US10/052899, dated Jan. 10, 2011.
Supplementary European Search Report for Application No. EP 05 80 2894, dated Jul. 27, 2011.
Supplementary European Search Report in Application No. 05 800 844, dated Aug. 19, 2011.
Supplementary European Search Report in Application No. EP 05 80 4291, dated Jul. 26, 2011.
Supplementary European Search Report in Application No. EP 05 85 8430, dated Aug. 18, 2011.
Supplementary European Serach Report for Application No. EP 08877338.7, dated Aug. 16, 2012.
Supplementary European Search Report for Application No. EP09819594.4, dated Aug. 14, 2012.
Non-Final Office Action for U.S. Appl. No. 11/236,908, mailed Mar. 25, 2006.
Final Office Action for U.S. Appl. No. 11/236,908, mailed May 17, 2011.
Non-final Office Action for U.S. Appl. No. 11/236,908, mailed Aug. 24, 2009.
Non-final Office Action for U.S. Appl. No. 11/236,977, mailed Aug. 3, 2009.
Final Office Action for U.S. Appl. No. 11/237,263, mailed Jul. 7, 2010.
Non-final Office Action for U.S. Appl. No. 1/237,263, mailed Oct. 7, 2009.
Final Office Action for U.S. Appl. No. 11/237,264, mailed Jun. 2, 2010.

(56) References Cited

OTHER PUBLICATIONS

Non-final Office Action for U.S. Appl. No. 11/237,264, mailed Oct. 5, 2009.
Final Office Action for U.S. Appl. No. 11/701,799, mailed Nov. 23, 2010.
Non-final Office Action for U.S. Appl. No. 11/237,420, mailed Mar. 5, 2009.
Final Office Action for U.S. Appl. No. 11/237,420, mailed Nov. 4, 2009.
Non-final Office Action for U.S. Appl. No. 11/237,420, mailed Dec. 6, 2010.
Non-final Office Action for U.S. Appl. No. 11/238,532, mailed Mar. 30, 2009.
Final Office Action for U.S. Appl. No. 11/238,532, mailed Sep. 9, 2009.
Final Office Action for U.S. Appl. No. 11/238,554, mailed May 12, 2010.
Non-final Office Action for U.S. Appl. No. 11/238,554, mailed Oct. 9, 2009.
Final Office Action for U.S. Appl. No. 11/238,554, mailed May 1, 2009.
Non-final Office Action for U.S. Appl. No. 11/238,554, mailed Jul. 25, 2008.
Non-final Office Action for U.S. Appl. No. 11/238,564, mailed Apr. 16, 2008.
Final Office Action for U.S. Appl. No. 11/238,564, mailed Aug. 6, 2009.
Non-final Office Action for U.S. Appl. No. 11/239,555, mailed Mar. 30, 2009.
Non-final Office Action for U.S. Appl. No. 11/525,328, mailed Apr. 30, 2007.
Non-final Office Action for U.S. Appl. No. 11/525,390, mailed Jul. 14, 2010.
Final Office Action for U.S, Appl. No. 11/525,390, mailed Feb. 21, 2011.
Final Office Action for U.S. Appl. No. 11/582,135, mailed May 12, 2011.
Non-final Office Action for U.S. Appl. No. 11/582,135, mailed Nov. 9, 2010.
Non-final Office Action for U.S. Appl. No. 11/582,135, mailed Jan. 6, 2010.
Non-final Office Action for U.S. Appl. No. 11/582,135, mailed May 12, 2009.
Non-final Office Action for U.S. Appl. No. 11/701,799, mailed Apr. 12, 2010.
Non-final Office Action for U.S. Appl. No. 11/978,840, mailed Dec. 3, 2010.
Non-final Office Action for U.S. Appl. No. 11/980,155, mailed Mar. 24, 2011.
Non-final Office Action for U.S. Appl. No. 12/075,223, mailed Dec. 8, 2010.
Non-final Office Action for U.S. Appl. No. 12/325,546, mailed Feb. 25, 2010.
Final Office Action for U.S. Appl. No. 12/325,546, mailed Aug. 31, 2010.
Non-final Office Action for U.S. Appl. No. 12/364,763, mailed Dec. 11, 2009.
Final Office Action for U.S. Appl. No. 12/364,763, mailed Sep. 21, 2010.
Interview summary for U.S. Appl. No. 11/236,908 mailed May 5, 2009.
Interview summary for U.S. Appl. No. 11/236,908 mailed Dec. 2, 2010.
Interview summary for U.S. Appl. No. 11/237,420 mailed May 5, 2009.
Interview summary for U.S. Appl. No. 11/582,135 mailed Dec. 7, 2010.
Interview summary for U.S. Appl. No. 12/325,546 mailed Dec. 2, 2010.
Interview summary for U.S. Appl. No. 12/364,763 mailed Dec. 2, 2010.
Final Office Action for U.S. Appl. No. 11/237,420, mailed Jul. 13, 2011.
Final Office Action for U.S. Appl. No. 11/978,840, mailed Jun. 22, 2011.
Final Office Action for U.S. Appl. No. 12/075,223, mailed Aug. 11, 2011.
Non-final Office Action for U.S. Appl. No. 11/525,390, mailed Jul. 11, 2011.
Non-Final Office Action for U.S. Appl. No. 11/701,799, mailed Aug. 17, 2011.
Non-Final Office Action for U.S. Appl. No. 11/582,135, mailed Oct. 14, 2011.
Final Office Action for U.S. Appl. No. 11/980,155, mailed Oct. 21, 2011.
Non-Final Office Action for U.S. Appl. No. 11/236,908, mailed Dec. 2, 2011.
Non-Final Office Action for U.S Appl. No. 12/182,261, mailed Dec. 21, 2011.
Non-Final Office Action for U.S. Appl. No. 12/401,243, mailed Jan. 5, 2012.
Notice of Allowance for U.S. Appl. No. 11/582,135, mailed Jan. 9, 2012.
Non-Final Office Action for U.S. Appl. No. 12/182,165, mailed Jan. 5, 2012.
Final Office Action for U.S. Appl. No. 11/701,799, mailed Feb. 13, 2012.
Non-Final Office Action for U.S. Appl. No. 12/581,582, mailed Mar. 14, 2012.
Final Office Action for U.S. Appl. No. 12/182,165, mailed Apr. 6, 2012.
Final Office Action for U.S. Appl. No. 12/182,261 mailed Apr. 30, 2012.
Notice of Allowance for U.S. Appl. No. 11/236,908, mailed May 11, 2012.
Final Office Action for U.S. Appl. No. 12/401,243, mailed Jun. 11, 2012.
Notice of Allowance for U.S. Appl. No. 12/182,261, mailed Jul. 23, 2012.
Advisory Action for U.S. Appl. No. 12/401,243, mailed Aug. 27, 2012.
Final Office Action for U.S. Appl. No. 12/581,582 mailed Aug. 29, 2012.
Ackman, R.G., "Fish Oils", *Bailey's Industrial Oil and Fat Products*, 6$^{th}$ Edition, 279-317 (2005).
Ahuja et al. Journal of Indian Pediatric Surgery 2002 7:15-20.
Andes, et al. "Antiproliferative Strategies for the Treatment of Vascular Proliferative Disease", *Current Vascular Pharmacology*, 1)1): 85-98 (2003).
A paper entitled "Evaluation of the Biocompatibility and Drug Delivery Capabilities of Biological Oil Based Stent Coatings" by Shengqio Li of the Katholieke Universiteit Leuven.
Jorge, N., "Grasas y Aceites", 48(1): 17-24, (1997).
Jonasson, Lena et al., "Cyclosporon A inhibits smooth muscle proliferation in the vascular response to injury," Proc. Natl. Acad. Sci. USA, vol. 85: 2303-2306 (1988).
Lipids, Chapter 19, pp. 1-12 (2002).
Ogunniyi, D.S., "Castor oil: A vital industrial raw material," Biosource Technology, vol. 97: 1086-1091 (2006).
Polymerization Merriam-Webster Online Dictionary, retrieved from <www.merriam-webster.com> on Dec. 13, 2009; Merriam-Webster's Inc. 2009; pp. 1.
Redman, L.V. et al., "The drying rate of raw paint oils—a comparison," The Journal of Industrial and Engineering Chemistry vol. 5: 630-636 (1913).
Rutkow, Ira M. et al., "Tension-free' inguinal herniorrhaphy: A preliminary report on the 'mesh plug' technique," Surgery, vol. 114:3-8 (1993).
Shahidi, Fereidoon ed.; "Bailey's Industrial Oil and Fats Products" 2005; John Wiley and Sons; vol. 5, Edible Oil and Fat Products: Processing Technologies, pp. 1-15.

(56) References Cited

OTHER PUBLICATIONS

Websters Dictionary Online, Accessed on Feb. 13, 2009, entry for "polymer" p. 1 of 1.
Winter, et al., "Physical and Chemical Gelation" *Encyclopedia of Materials—Science and Technology*, vols. 1-11: 6691-6999 (2001).
International Search Report for International Application No. PCT/US05/34941, dated May 4, 2006.
International Search Report for PCT/US2011/44292, dated Dec. 6, 2011.
Supplementary European Search Report for Application No. EP 12004057, dated Apr. 10, 2013.
International Search Report for International Application PCT/US2013/044653, dated Sep. 4, 2013.
Notice of Allowance for U.S. Appl. No. 11/525,390, mailed Oct. 4, 2012.
Advisory Action for U.S. Appl. No. 12/581,582, dated Nov. 14, 2012.
Notice of Allowance for U.S. Appl. No. 11/525,390, dated Nov. 20, 2012.
Notice of Allowance for U.S. Appl. No. 11/525,390, mailed Nov. 30, 2012.
Non-Final Office Action for U.S. Appl. No. 13/404,487, dated Dec. 20, 2012.
Non-Final Office Action for U.S. Appl. No. 13/184,512, dated Jan. 31, 2013.
Non-Final Office Action for U.S. Appl. No. 11/978,840, dated Feb. 19, 2013.
Non-Final Office Action for U.S. Appl. No. 13/682,991, dated Mar. 18, 2013.
Notice of Allowance for U.S. Appl. No. 13/404,487, dated Apr. 2, 2013.
Non-Final Office Action for U.S. Appl. No. 11/236,943, dated Apr. 22, 2013.
Final Office Action for U.S. Appl. No. 13/184,512, date Jun. 25, 2013.
Non-Final Office Action for U.S. Appl. No. 13/593,656, dated Jul. 15, 2013.
Notice of Allowance for U.S. Appl. 13/682,991, dated Aug. 1, 2013.
Notice of Allowance for U.S. Appl. No. 11/978,840, dated Aug. 6, 2013.
Mallegol, "Long-Term Behavior of Oil-Based Varnishes and Paints Photo-and Thermooxidation of Cured Linseed Oil", *Journal of the American Oil Chemists' Society*, 77:257-263 (2000).
Non-Final Office Action for U.S. Appl. No. 11/237,420, dated Nov. 12, 2013.
Non-Final Office Action for U.S. Appl. No. 12/075,223, dated Nov. 12, 2013.
Non-Final Office Action for U.S. Appl. No. 11/980,155, dated Nov. 12, 2013.
Notice of Allowance for U.S. Appl. No. 13/593,656, dated Jan. 24, 2014.
Final Office Action for U.S. Appl. No. 11/236,943, dated Dec. 4, 2013.
Notice of Allowance for U.S. Appl. No. 11/237,263 (listed on SB-08 as U.S. Publication No. US-2006-0110457), dated Mar. 27, 2014.
Supplementary European Search Report for Application No. EP 10825447, dated Mar. 31, 2014.
Non Final Office Action for U.S. Appl. No. 12/325,546 (listed on SB-08 as U.S. Publication No. US-2009-0181937), dated Apr. 22, 2014.
Non Final Office Action for U.S. Appl. No. 12/364,763 (listed on SB-08 as U.S. Publication No. US-2009-0208552), dated Apr. 23, 2014.
Non Final Office Action for U.S. Appl. No. 12/401,243 (listed on SB/08 as US 2010-0233232), mailed May 8, 2014.
Non Final Office Action for U.S. Appl. No. 12/581,582 (listed on SB-08 as U.S. Publication 2010-0183697), dated May 29, 2014.

\* cited by examiner

STAND-ALONE FILM AND METHODS FOR MAKING THE SAME

RELATED APPLICATION

This application claims priority to, and the benefit of, U.S. Provisional Application No. 60/613,808, filed on Sep. 28, 2004. This application also relates to co-pending U.S. patent application Ser. No. 11/237,420, filed concurrently with this application on Sep. 28, 2005. The disclosure of the above-mentioned application is hereby incorporated by reference herein in its entirety.

FIELD OF THE INVENTION

The present invention generally relates to stand-alone films, and more particularly to stand-alone films that are formed from fatty acids.

BACKGROUND OF THE INVENTION

Different surgical procedures often make use of a method referred to as blunt dissection. Blunt dissection can be generally described as dissection accomplished by separating tissues along natural cleavage lines without cutting. Blunt dissection is executed using a number of different blunt surgical tools, as is understood by those of ordinary skill in the art. Blunt dissection is often performed in cardiovascular, colo-rectal, urology, gynecology, upper GI, and plastic surgery applications, among others.

In accordance with several methods of blunt dissection, a small incision is made in the patient. Specially designed blunt dissection tools having small profiles are inserted through the incision to the desired location in the body. Longer tools may be used to access locations substantially distal from the incision, while shorter tools can be used to access locations closer to the incision.

After the blunt dissection separates the desired tissues into separate areas, there is often a need to maintain the separation of those tissues. In fact, post surgical adhesions can occur following almost any type of surgery, resulting in serious postoperative complications. Adhesions may cause intestinal obstruction, bowel torsion, pain and infertility following general abdominal and pelvic surgery. Adhesions can also develop following orthopedic and cardiac surgery. Surgical adhesion disease is a complex inflammatory disease in which tissues that normally remain separated in the body grow into each other as a result of surgical trauma. Conventional surgical methods make use of anti-adhesion barriers, such as Interceed® from Johnson & Johnson or Seprafilm® from Genzyme Corporation.

Interceed® is a fabric relatively easy to apply and handle. However, effectiveness may be diminished when bleeding has not been completely controlled. Seprafilm® is widely used in general surgery. However, it is challenging for surgeons to apply and handle because of the film's tendency to easily break apart upon exposure to water due to their chemical make up and bio-dissolvable properties. The composition and structural properties of these bio-dissolvable products require that they be handled with dry hands or instruments, which can be difficult during most surgical intervention operations. Furthermore, many of these bio-dissolvable films are made intentionally thin to minimize tissue disruption and consequently end up being structurally weak (i.e., easily torn or folded during handling). In addition, Seprafilm® is composed of two chemically modified biopolymers, sodium hyaluronate (HA) and carboxymethylcellulose (CMC), reacted with an activating agent 1-(3-dimethylaminopropyl)-3-ethylcarbodiimide hydrochloride (EDC) to form a water insoluble powder, hyaluronic acid-carboxymethylcellulose (HA-CMC). Although it is biodegradable, some of its breakdown products, such as smaller CMC units and ethyl-(3-dimethylaminopropyl)-urea (EDU), are not consumable by the patient's cell tissues. Hence, biodegradable substances, such as polymers, can cause inflammatory response due to either the parent substance or those substances formed during breakdown, and they may or may not be absorbed by tissues.

SUMMARY OF THE INVENTION

The present invention relates to a bio-absorbable stand-alone film that can exhibit anti-inflammatory properties, non-inflammatory properties, and anti-adhesion properties, and the corresponding method of making. The stand-alone film is generally formed of a naturally occurring oil, or an oil composition formed in part of a naturally occurring oil. In addition, the oil composition can include a therapeutic agent component, such as a drug or other bioactive agent. The stand-alone film is implantable in a patient for short term or long term applications. As implemented herein, the stand-alone film is a non-polymeric cross-linked gel derived at least in part from a fatty acid compound.

It should be noted that the term cross-linked gel, as utilized herein with reference to the present invention, refers to a gel that is non-polymeric and is derived from an oil composition comprising molecules covalently cross-linked into a three-dimensional network by one or more of ester, ether, peroxide, and carbon-carbon bonds in a substantially random configuration. In various preferred embodiments, the oil composition comprises a fatty acid molecule, a glyceride, and combinations thereof.

In accordance with one embodiment of the present invention, a stand-alone film includes a non-polymeric cross-linked gel material formed at least in part of a fatty acid compound or derivative or analog thereof.

In accordance with aspects of the present invention, the fatty acid compound includes omega-3 fatty acid, fish oil fatty acid, free fatty acid, triglycerides, esters of fish oil, or a combination thereof. The fish oil fatty acid can include one or more of arachidic acid, gadoleic acid, arachidonic acid, eicosapentaenoic acid, docosahexaenoic acid or derivatives, analogs and pharmaceutically acceptable salts thereof. The free fatty acid can include one or more of butyric acid, caproic acid, caprylic acid, capric acid, lauric acid, myristic acid, palmitic acid, palmitoleic acid, stearic acid, oleic acid, vaccenic acid, linoleic acid, alpha-linolenic acid, gamma-linolenic acid, behenic acid, erucic acid, lignoceric acid, analogs and pharmaceutically acceptable salts thereof.

In accordance with further aspects of the present invention, the stand-alone film further includes a vitamin E compound forming a portion of the fatty acid compound. The vitamin E compound can include one or more of alpha-tocopherol, beta-tocopherol, delta-tocopherol, gamma-tocopherol, alpha-tocotrienol, beta-tocotrienol, delta-tocotrienol, gamma-tocotrienol, alpha-tocopherol acetate, beta-tocopherol acetate, gamma-tocopherol acetate, delta-tocopherol acetate, alpha-tocotrienol acetate, beta-tocotrienol acetate, delta-tocotrienol acetate, gamma-tocotrienol acetate, alpha-tocopherol succinate, beta-tocopherol succinate, gamma-tocopherol succinate, delta-tocopherol succinate, alpha-tocotrienol succinate, beta tocotrienol succinate, delta-tocotrienol succinate, gamma-tocotrienol succinate, mixed tocopherols, vitamin E TPGS, derivatives, analogs and pharmaceutically acceptable salts thereof.

In accordance with further aspects of the present invention, the fatty acid compound or derivative or analog thereof is cured to increase viscosity to form the film. The stand-alone film is cured using at least one curing method selected from a group of curing methods including application of UV light, application of heat, airflow, and reaction with a gas or chemical cross-linker. It should be noted that curing with respect to the present invention generally refers to thickening, hardening, or drying of a material brought about by heat, UV, or chemical means.

In accordance with further aspects of the present invention, the stand-alone film further includes a therapeutic agent. The therapeutic agent can include an agent selected from the group consisting of antioxidants, anti-inflammatory agents, anti-coagulant agents, drugs to alter lipid metabolism, anti-proliferatives, anti-neoplastics, tissue growth stimulants, functional protein/factor delivery agents, anti-infective agents, imaging agents, anesthetic agents, chemotherapeutic agents, tissue absorption enhancers, anti-adhesion agents, germicides, analgesics, prodrugs, and antiseptics.

In accordance with further aspects of the present invention, the therapeutic agent is combined with the fatty acid compound prior to formation of the film, resulting in the therapeutic agent being interspersed throughout the film. Alternatively, the therapeutic agent is applied to the film in the form of a coating.

In accordance with further aspects of the present invention, the stand-alone film is bioabsorbable. The stand-alone film can further maintain anti-adhesive properties.

In accordance with another embodiment of the present invention, a method of forming a stand-alone film is introduced. The method includes providing a chamber formed of flexible porous material and having an internal wall and filling the chamber with a fatty acid compound in liquid form. The method also includes curing the fatty acid compound proximal to the internal wall to form a film along the internal wall. The method further includes removing the fatty acid compound that remains in liquid form and separating the film from the internal wall of the flexible porous material creating a stand-alone film. In accordance with one aspect of the present invention, the flexible material includes expanded polytetrafluoroethylene (ePTFE).

In accordance with further aspects of the present invention, the fatty acid compound includes omega-3 fatty acid, fish oil fatty acid, free fatty acid, triglycerides, esters of fish oil, or a combination thereof. The fish oil fatty acid can include one or more of arachidic acid, gadoleic acid, arachidonic acid, eicosapentaenoic acid, docosahexaenoic acid or derivatives, analogs and pharmaceutically acceptable salts thereof. The free fatty acid can include one or more of butyric acid, caproic acid, caprylic acid, capric acid, lauric acid, myristic acid, palmitic acid, palmitoleic acid, stearic acid, oleic acid, vaccenic acid, linoleic acid, alpha-linolenic acid, gamma-linolenic acid, behenic acid, erucic acid, lignoceric acid, analogs and pharmaceutically acceptable salts thereof.

In accordance with further aspects of the present invention, the method further includes mixing a vitamin E compound to form a portion of the fatty acid compound. The vitamin E compound can include one or more of alpha-tocopherol, beta-tocopherol, delta-tocopherol, gamma-tocopherol, alpha-tocotrienol, beta-tocotrienol, delta-tocotrienol, gamma-tocotrienol, alpha-tocopherol acetate, beta-tocopherol acetate, gamma-tocopherol acetate, delta-tocopherol acetate, alpha-tocotrienol acetate, beta-tocotrienol acetate, delta-tocotrienol acetate, gamma-tocotrienol acetate, alpha-tocopherol succinate, beta-tocopherol succinate, gamma-tocopherol succinate, delta-tocopherol succinate, alpha-tocotrienol succinate, beta-tocotrienol succinate, delta-tocotrienol succinate, gamma-tocotrienol succinate, mixed tocopherols, vitamin E TPGS, derivatives, analogs and pharmaceutically acceptable salts thereof.

In accordance with further aspects of the present invention, the curing includes using at least one curing method selected from a group of curing methods including application of UV light, application of heat, airflow, and reaction with a gas or chemical cross-linker.

In accordance with further aspects of the present invention, the method further includes combining a therapeutic agent with the fatty acid compound. The therapeutic agent can be combined with the fatty acid compound prior to formation of the stand-alone film, interspersing the therapeutic agent throughout the stand-alone film. Alternatively, a therapeutic agent can be applied to the stand-alone film in the form of a coating.

In accordance with still another embodiment of the present invention, another method of forming a stand-alone film is introduced. The method includes providing a fatty acid compound in liquid form and applying the fatty acid compound to a substrate. The method also includes curing the fatty acid compound to form the stand-alone film. In accordance with one aspect of the present invention, the substrate includes expanded polytetrafluoroethylene (ePTFE) or polytetrafluoroethylene (PTFE).

In accordance with further aspects of the present invention, the fatty acid compound includes omega-3 fatty acid, fish oil fatty acid, free fatty acid, triglycerides, esters of fish oil, or a combination thereof. The fish oil fatty acid can include one or more of arachidic acid, gadoleic acid, arachidonic acid, eicosapentaenoic acid, docosahexaenoic acid or derivatives, analogs and pharmaceutically acceptable salts thereof. The free fatty acid can include one or more of butyric acid, caproic acid, caprylic acid, capric acid, lauric acid, myristic acid, palmitic acid, palmitoleic acid, stearic acid, oleic acid, vaccenic acid, linoleic acid, alpha-linolenic acid, gamma-linolenic acid, behenic acid, erucic acid, lignoceric acid, analogs and pharmaceutically acceptable salts thereof.

In accordance with further aspects of the present invention, the method further includes mixing a vitamin E compound to form a portion of the fatty acid compound. The vitamin E compound can include one or more of alpha-tocopherol, beta-tocopherol, delta-tocopherol, gamma-tocopherol, alpha-tocotrienol, beta-tocotrienol, delta-tocotrienol, gamma-tocotrienol, alpha-tocopherol acetate, beta-tocopherol acetate, gamma-tocopherol acetate, delta-tocopherol acetate, alpha-tocotrienol acetate, beta-tocotrienol acetate, delta-tocotrienol acetate, gamma-tocotrienol acetate, alpha-tocopherol succinate, beta-tocopherol succinate, gamma-tocopherol succinate, delta-tocopherol succinate, alpha-tocotrienol succinate, beta-tocotrienol succinate, delta-tocotrienol succinate, gamma-tocotrienol succinate, mixed tocopherols, vitamin E TPGS, derivatives, analogs and pharmaceutically acceptable salts thereof.

In accordance with further aspects of the present invention, the curing includes using at least one curing method selected from a group of curing methods including application of UV light and application of heat. The UV light can also be applied to set the fatty acid compound by forming a skin on the top surface of the fatty acid compound in liquid form prior to additional curing.

In accordance with further aspects of the present invention, the method further includes combining a therapeutic agent with the fatty acid compound. A therapeutic agent can be combined with the fatty acid compound prior to formation of the stand-alone film, interspersing the therapeutic agent throughout the stand-alone film. Alternatively, a therapeutic agent can be applied to the stand-alone film in the form of a coating.

In accordance with another aspect of the present invention, the method further includes treating the fatty acid compound in liquid form prior to application to the substrate to form a pre-thickened fatty acid compound.

In accordance with further aspects of the present invention, the substrate has an indentation that is used as a mold to shape the stand-alone film. Alternatively, the method can further include the step of cutting the film to a desirable shape.

In accordance with yet another aspect of the present invention, a barrier layer includes a non-polymeric cross-linked gel formed at least in part of a fatty acid compound or derivative or analog thereof.

In accordance with aspects of the present invention, the fatty acid compound includes omega-3 fatty acid, fish oil fatty acid, free fatty acid, triglycerides, esters of fish oil, or a combination thereof. The barrier layer can further include a therapeutic agent. The therapeutic agent includes an agent selected from the group consisting of antioxidants, anti-inflammatory agents, anti-coagulant agents, drugs to alter lipid metabolism, anti-proliferatives, anti-neoplastics, tissue growth stimulants, functional protein/factor delivery agents, anti-infective agents, imaging agents, anesthetic agents, chemotherapeutic agents, tissue absorption enhancers, anti-adhesion agents, germicides, analgesics, prodrugs, and antiseptics.

In accordance with still another embodiment of the present invention, a method of using a stand-alone film includes placing a stand-alone film in between two body tissues, wherein the stand-alone film is formed at least in part of a fatty acid compound or derivative or analog thereof.

BRIEF DESCRIPTION OF THE DRAWINGS

The present invention will become better understood with reference to the following description and accompanying drawings, wherein.

DETAILED DESCRIPTION

The present invention utilizes primarily fatty acids to form a stand-alone film. The phrase stand-alone film is used herein to refer to a film that does not require any additional material to provide structure to the film. A medical device having a coating of fish oil is not a stand-alone film because the coating of fish oil relies on the device to provide structure to the film. The stand-alone films are bioabsorbable and cells may consume the breakdown products, fatty acid, short and long chain alcohol, and glyceride molecules. Bioabsorbable substances break down into substances or components that do not cause an inflammatory response and can be consumed by the cells forming the body tissues. Furthermore, the resultant film is flexible, easy to handle, and relatively strong. The resultant film may be used with many surgical procedures when anti-adhesion is desirable for a pre-determined amount of time.

Figure 1A:
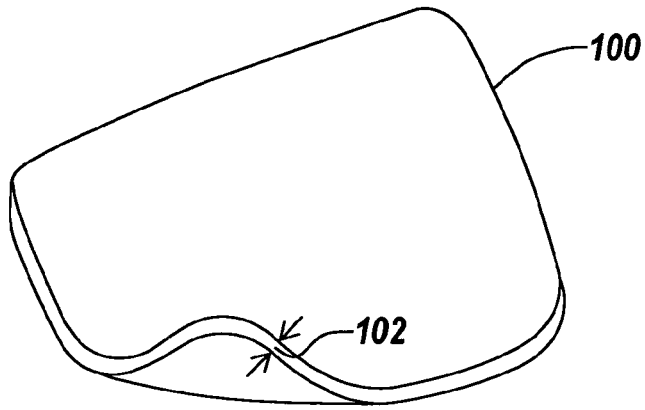
FIG. 1A is an exemplary illustration of a stand-alone film according to one embodiment of the present invention.

FIGS. 1A through 10 illustrate example embodiments of a non-polymeric stand-alone film and the method of making according to the present invention. FIG. 1A illustrates an exemplary stand-alone film 100 according to one embodiment of the present invention. The stand-alone film 100 is flexible, to the extent that it can be placed in a flat, curved, or rolled configuration within a patient. The stand-alone-film 100 is implantable, for both short term and long term applications. The stand-alone film 100 has a thickness 102 in the range of 0.003 inches to 0.008 inches. One of ordinary skill in the art will appreciate that thicker films may be made from layering several stand-alone films 100 together, or the film itself may be made thicker. Thickness 102 is positively proportional to the time it takes for the stand-alone film 100 to breakdown in a patient's body. In other words, the thicker the stand-alone film 100 is, the longer it takes for the stand-alone film 100 to completely breakdown in the patient's body. The stand-alone film 100 may be constructed to provide a barrier for a predetermined period of time, such as, but not limited to, a period of hours, a period of weeks, or a period of months.

Stand-alone film 100 is made from fatty acids, such as omega-3 fatty acid, fish oil fatty acid, free fatty acid, triglycerides, esters of fish oil, or a combination thereof. Fish oil fatty acid may further be one or a combination of arachidic acid, gadoleic acid, arachidonic acid, eicosapentaenoic acid, docosahexaenoic acid or derivatives, analogs, and pharmaceutically acceptable salts thereof. Free fatty acid may be one or more of butyric acid, caproic acid, caprylic acid, capric acid, lauric acid, myristic acid, palmitic acid, palmitoleic acid, stearic acid, loeic acid, vaccenic acid, linoleic acid, alpha-linolenic acid, gamma-linolenic acid, behenic acid, erucic acid, lignoceric acid, or derivatives, analogs and pharmaceutically acceptable salts thereof.

More specifically, the stand-alone film 100 is formed of a non-polymeric cross-linked gel derived from fatty acid compounds. The fatty acids include omega-3 fatty acids when the oil utilized to form the stand-alone film is fish oil or an analog or derivative thereof. As liquid fish oil is heated, autoxidation occurs with the absorption of oxygen into the fish oil to create hydroperoxides in an amount dependent upon the amount of unsaturated (C=C) sites in the fish oil. However, the (C=C) bonds are not consumed in the initial reaction. Concurrent with the formation of hydroperoxides is the isomerization of (C=C) double bonds from cis to trans in addition to double bond conjugation. It has been demonstrated that hydroperoxide formation increases with temperature. Heating of the fish oil allows for cross-linking between the fish oil unsaturated chains using a combination of peroxide (C—O—O—C), ether (C—O—C), and hydrocarbon (C—C) bridges. The formation of the cross-links results in gelation of the film after the (C=C) bonds have substantially isomerized into the trans configuration. The (C=C) bonds can also form C—C cross-linking bridges in the glyceride hydrocarbon chains using a Diels-Alder Reaction. In addition to solidifying the film through cross-linking, both the hydroperoxide and (C=C) bonds can undergo secondary reactions converting them into lower molecular weight secondary oxidation byproducts including aldehydes, ketones, alcohols, fatty acids, esters, lactones, ethers, and hydrocarbons.

Accordingly, the film derived from fatty acid compounds, such as those of fish oil, includes a cross-linked structure of triglyceride and fatty acid molecules in addition to free and bound glycerol, monoglyceride, diglyceride, and triglyceride, fatty acid, anhydride, lactone, aliphatic peroxide, aldehyde, and ketone molecules. There are a substantial amount of ester bonds remaining after curing in addition to peroxide linkages forming the majority of the cross-links in the film. The film degrades into fatty acid, short and long chain alcohol, and glyceride molecules, which are all non-inflammatory and likewise consumable by cells in the soft tissue to which the film is applied. Thus, the film is bioabsorbable.

The stand-alone film 100 further provides a lubricious and anti-adhesive surface against tissue. The stand-alone film itself, in its substantially cured configuration, can provide a physical anti-adhesion barrier between two sections of tissue. The use of the naturally occurring oil, such as fish oil, provides extra lubrication to the surface of the film, which helps to reduce injury. With less injury, there is less of an inflammatory response, and less healing required. The oily surface of the film provides the anti-adhesion characteristics. One of ordinary skill in the art will appreciate that different oils will have different anti-adhesive properties, and the oils can be modified to be more liquefied or more solid or waxy, as desired. Accordingly, the degree of anti-adhesive properties offered by the film can vary. The modification of the oils from a more liquid physical state to a more solid, but still flexible, physical state is implemented through the curing process. As the oils are cured, especially in the case of fatty acid-based oils such as fish oil, cross-links form creating a gel. As the curing process is performed over increasing time durations and/or increasing temperature conditions and/or increasing UV output, more cross-links form transitioning the gel from a relatively liquid gel to a relatively solid-like, but still flexible, gel structure.

In accordance with one aspect of the present invention, the stand-alone film 100 can further include a therapeutic agent. The therapeutic agent can include an agent selected from the group consisting of antioxidants, anti-inflammatory agents, anti-coagulant agents, drugs to alter lipid metabolism, anti-proliferatives, anti-neoplastics, tissue growth stimulants, functional protein/factor delivery agents, anti-infective agents, imaging agents, anesthetic agents, chemotherapeutic agents, tissue absorption enhancers, anti-adhesion agents, germicides, analgesics, prodrugs, and antiseptics. The therapeutic agent may be added to the fatty acid compound prior to forming a stand-alone film so that the therapeutic agent is interspersed throughout the stand-alone film 100. Alternatively, the therapeutic agent may be applied to the stand-alone film 100 to form a coating on a surface of the stand-alone film after the fatty acid compound has formed a stand-alone film.

In accordance with one aspect of the present invention, the therapeutic agent can include a vitamin E compound. The vitamin E compound may include one or more of alpha-tocopherol, beta-tocopherol, delta-tocopherol, gamma-tocopherol, alpha-tocotrienol, beta-tocotrienol, delta-tocotrienol, gamma-tocotrienol, alpha-tocopherol acetate, beta-tocopherol acetate, gamma-tocopherol acetate, delta-tocopherol acetate, alpha-tocotrienol acetate, beta-tocotrienol acetate, delta-tocotrienol acetate, gamma-tocotrienol acetate, alpha-tocopherol succinate, beta-tocopherol succinate, gamma-tocopherol succinate, delta-tocopherol succinate, alpha-tocotrienol succinate, beta-tocotrienol succinate, delta-tocotrienol succinate, gamma-tocotrienol succinate, mixed tocopherols, vitamin E TPGS, derivatives, analogs and pharmaceutically acceptable salts thereof.

One of ordinary skill in the art will appreciate that the stand-alone film of the present invention may be applied with other therapeutic agents that are not listed above. These therapeutic agents are added for healing purposes and not to provide structure to the stand-alone film. Furthermore, the stand-alone film can be formed in a manner that creates the potential for controlled long term release of a therapeutic agent, while still maintaining the benefits of the natural oil component of the film. With the present invention, and in the field of soft tissue applications, the uptake of the therapeutic agent is facilitated by the delivery of the therapeutic agent to the cell membrane by the bio-absorbable stand-alone film.

Figure 1B:
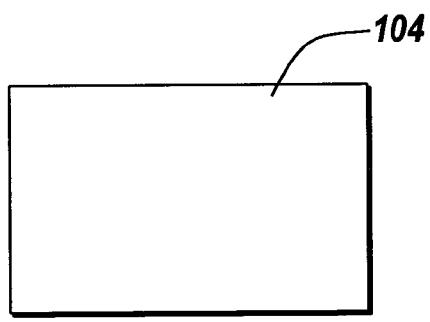
FIG. 1B is an exemplary top-view illustration of a rectangular shaped stand-alone film in accordance with one embodiment of the present invention.
Figure 1D:
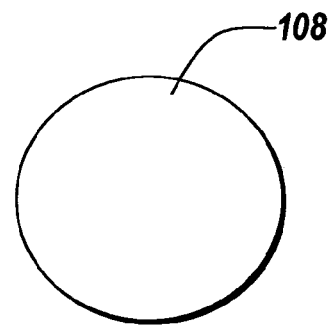
FIG. 1D is an exemplary top-view illustration of a circular shaped stand-alone film in accordance with one embodiment of the present invention.
Figure 1C:
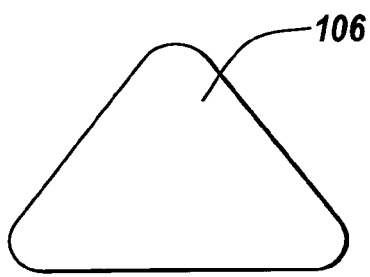
FIG. 1C is an exemplary top-view illustration of a triangular shaped stand-alone film in accordance with one embodiment of the present invention.
Figure 1E:
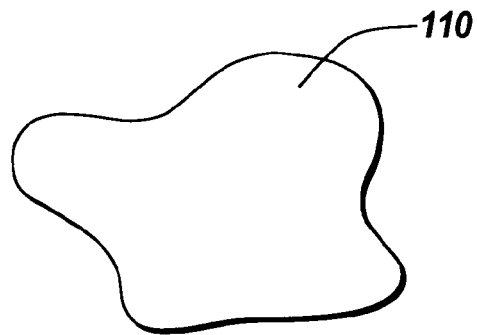
FIG. 1E is an exemplary top-view illustration of a custom shaped stand-alone film in accordance with one embodiment of the present invention.

The stand-alone film 100 can be formed in many different shapes. In accordance with one aspect of the present invention, the stand-alone film 100 can have a rectangular shape with square corners as illustrated in FIG. 1B. In accordance with another aspect of the present invention, the stand-alone film 100 can have a triangular shape with round corners as illustrated in FIG. 1C. In accordance with still another aspect of the present invention, the stand-alone film 100 can have a circular shape as illustrated in FIG. 1D. In accordance with yet another aspect of the present invention, the stand-alone film 100 can have a custom shape as illustrated in FIG. 1E.

One of ordinary skill in the art will appreciate that the present invention is not limited to the specific shapes and dimensions that are disclosed herein and the illustrative embodiments are merely for demonstration purposes only.

Figure 2:
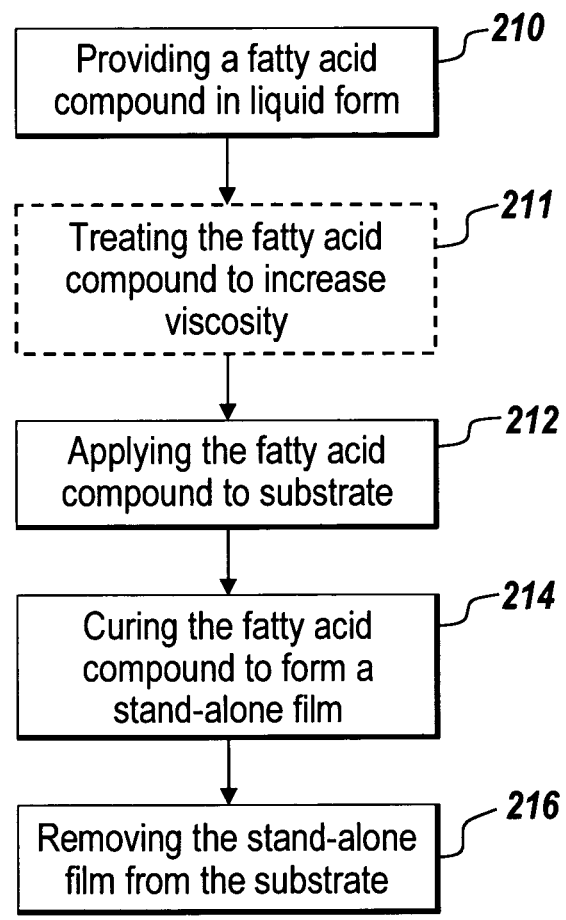
FIG. 2 is a flowchart illustrating a method of creating a stand-alone film from fatty acid compound in liquid form according to another embodiment of the present invention.

FIG. 2 is a flowchart illustrating a method of creating a stand-alone film from a fatty acid compound in liquid form according to one embodiment of the present invention. A fatty acid compound in liquid form is provided in step 210. Depending on the type of substrate used, the fatty acid compound is optionally treated to increase viscosity in step 211.

The viscosity of the fatty acid compound is raised to the point where the thickened fatty acid compound can be cast onto the substrate without the risk of immediate pooling or running of the fatty acid compound. The fatty acid compound is then applied to a substrate in step 212. If the fatty acid compound is in liquid form, the fatty acid compound may simply be poured onto the substrate. Instruments can be used to help spread the fatty acid compound on the substrate surface. If the fatty acid compound is of increased viscosity, the fatty acid compound can be applied to a substrate with the assistance of a casting knife. One of ordinary skill in the art will appreciate that there are many methods to apply compounds on to a substrate, and the specific methods mentioned here are not meant to limit the scope of the present invention. The fatty acid compound on the substrate is then treated to form a stand-alone film in step 214. The treating methods can include, but are not limited to, application of UV light, application of heat, airflow, and reaction with a gas or chemical cross-linker. For example, airflow of 0 to 1500 cfm may be applied across the surface of the fatty acid compound to form a stand-alone film. In another example, gases, such as oxygen and fluorine, and chemical cross-linkers, such as palladium as a catalyst, cobalt drier, alkyd mediums, manganese, and nickel, zinc, other oxidizing metals, organic peroxides, acid or base catalysts, and montmorillonite clay catalyst, can be used to react with the fatty acid compound to form a stand-alone film. Lastly, the stand-alone film is removed from the substrate in step 216. FIGS. 3A-3D are exemplary substrates that are suitable to practice one embodiment of the present invention using the flowchart in FIG. 2.

Figure 3A:
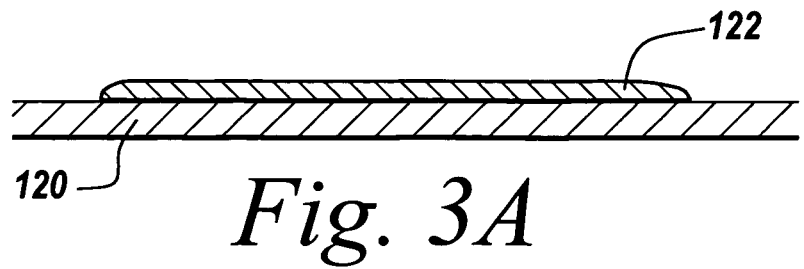
FIG. 3A is a cross-sectional illustration of a fatty acid compound disposed on top of a flat substrate according to one embodiment of the present invention.

FIG. 3A is a cross-sectional illustration of a fatty acid compound disposed on top of a flat substrate according to one embodiment of the present invention. In the embodiment, fatty acid compound 122 is pre-treated to increase the viscosity of the fatty acid compound 122 until a gelation process of the fatty acid compound 122 has started. The thickened fatty acid compound 122 is then applied directly on top of a flat non-porous substrate 120 using a controlled applicator, such as micrometer controlled film casting knife, spin casting, and the like. The flat non-porous substrate 120 with the thickened fatty acid compound 122 on top is then subjected to UV light exposure for a short period of time, such as, about 10-20 minutes, to set the film and prevent running of the fatty acid compound 122 at the elevated curing temperature. The fatty acid compound 122 on the flat non-porous substrate is then placed into an oven for a period of time at a set temperature, such as, a minimum of 12 hours at 200° F., to complete the curing process. The resultant film is removed from the flat non-porous substrate 120 to form a stand-alone film.

Figure 3B:
FIG. 3B is an exemplary Petri dish that is suitable for use in forming the stand-alone film in accordance with one embodiment of the present invention.
Figure 3C:
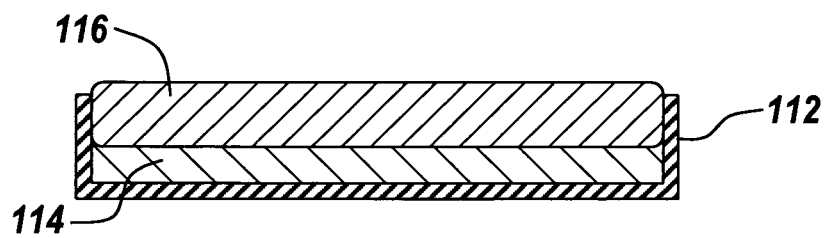
FIG. 3C is a cross-sectional illustration of a fatty acid compound disposed in a Petri dish with a cover according to one embodiment of the present invention.

FIG. 3B is an exemplary Petri dish that is suitable to practice one embodiment of the present invention. Petri dish 112 is a shallow cylindrical dish made of plastic or glass. The Petri dish 112 is filled half way with fatty acid compound 114 and then covered with a cover 116 made of porous material, such as shown in FIG. 3C. The Petri dish 112 is turned upside down (cover 116 side down) and placed into an oven. The temperature of the oven can be between 100° F. and 250° F. The Petri dish is left in the oven for a desired amount of time at a set temperature, such as a minimum of 12 hours at 200° F. After the Petri dish 112 has been in the oven for the desired amount of time, the Petri dish 112 is removed from the oven and kept upside down to allow the fatty acid compound 114 to cool to room temperature. When the fish oil has sufficiently cooled, the cover 116 is pierced near the edge to allow excess fish oil to drain out. Thus, a semi-cured layer of film is left behind on the cover 116. The Petri dish 112, along with the cover 116 and the semi-cured film are then placed back into the oven for a predetermined amount of time at a set temperature, such as a minimum of 4 hours at 200° F. to finish the curing process. After the film is completely cured, the Petri dish 112 is removed from the oven and allowed to cool. When the Petri dish 112 is cooled, the cover 116 is removed from the dish and the film is peeled away from the cover 116 to form a stand-alone film.

Figure 3D:
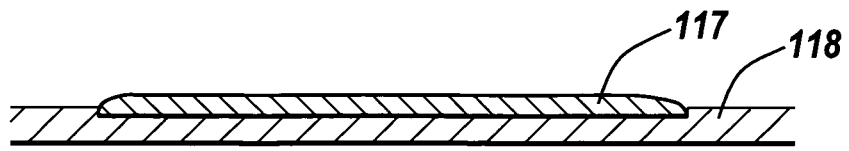
FIG. 3D is a cross-sectional illustration of a fatty acid compound disposed in a mold according to one embodiment of the present invention.

FIG. 3D is a cross-sectional illustration of a fatty acid compound disposed in a mold. Mold 118 is a flat substrate with a slight indentation into which the fatty acid compound 117 is applied.

One of ordinary skill in the art will appreciate that the mold may be used to shape the resultant stand-alone film. Additionally, patterns or words may be included in the mold to identify certain properties or features of the stand-alone films, such as names of one or more therapeutic agents that are included in the film, or the side of the film that has a coating of one or more therapeutic agents, thickness of the film, name of the company that produces the films, and etc.

One of ordinary skill in the art will also appreciate that sheets of stand-alone films can be cut to different shapes prior to shipping the stand-alone films to customers. In this manner, customers can choose to purchase different shapes of films for different purposes. This provides the surgeons the convenience to use pre-cut films that are suitable for different surgeries.

Figure 4:
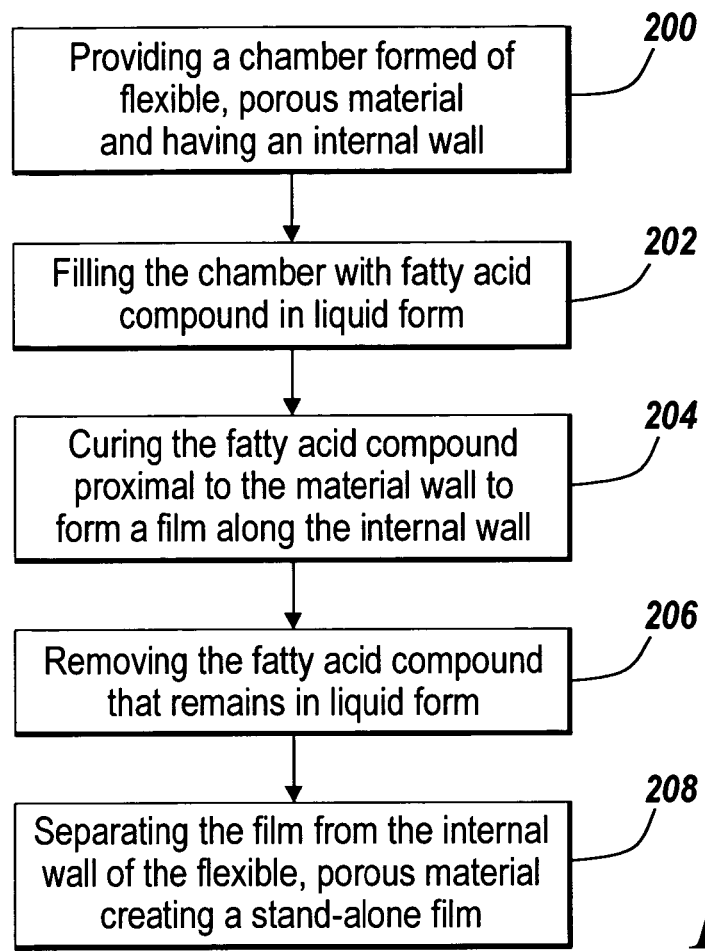
FIG. 4 is a flowchart illustrating a method of creating a stand-alone film from fatty acid compound in liquid form according to one embodiment of the present invention.
Figure 5:
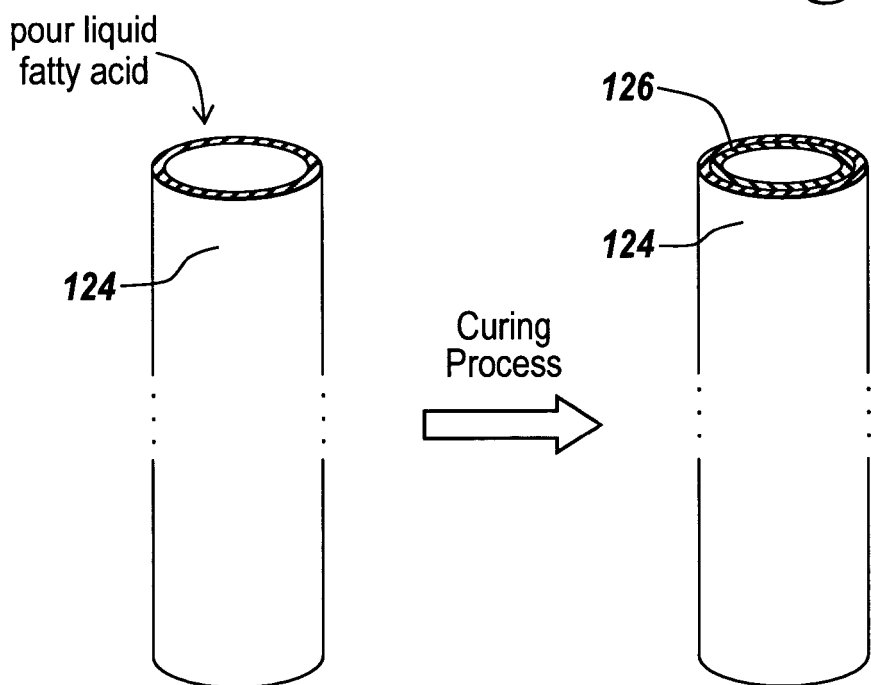
FIG. 5 is another illustration of a stand-alone film formed from using a tube substrate according to one embodiment of the present invention.

FIG. 4 is a flowchart illustrating a method of creating a stand-alone film using a tube structure, such as shown in FIG. 5. In step 200, a chamber formed of flexible porous material and having an internal wall, such as tube structure 124, is provided. The chamber is filled with fatty acid compound in liquid form in step 202. The tube is heated, such as at 100° F. to 300° F. in an oven for a desired amount of time, such as 12 hours to 6 weeks. The fatty acid compound is cured proximal to the internal wall of the chamber to form a film along the internal wall in step 204. As shown in FIG. 5, a thin film 126 is formed on the internal wall of the tube structure 124. Any excess fatty acid compound in liquid form is removed in step 206. For example, excess fatty acid compound in liquid form may be drained or poured out from tube structure 124. The film formed along the internal wall of the tube structure is separated from the internal wall to create a stand-alone film in step 208. One of ordinary skill in the art will appreciate that any tubing material that is flexible and porous, yet not allow liquid to penetrate, may be used in the present invention, such as expanded polytetrafluoroethylene and expanded Ultra High Molecular Weight Polyethylene.

One form of fatty acid is omega-3 fatty acid, which can act as an anti-inflammatory agent. Other therapeutic agents may also be utilized to enhance this feature. Therapeutic agents may also be added to a stand-alone film made of fatty acids to provide additional healing functions, such as through drug loading or drug coating.

As utilized herein, the phrase "therapeutic agent(s)" refers to a number of different drugs or agents available, as well as future agents that may be beneficial for use with the stand-alone film of the present invention. The therapeutic agent can take a number of different forms including anti-oxidants, anti-inflammatory agents, anti-coagulant agents, drugs to alter lipid metabolism, anti-proliferatives, anti-neoplastics, tissue growth stimulants, functional protein/factor delivery agents, anti-infective agents, anti-imaging agents, anesthetic agents, therapeutic agents, tissue absorption enhancers, anti-adhesion agents, germicides, anti-septics, analgesics, pro-drugs, and any additional desired therapeutic agents such as those listed in Table 1 below.

TABLE 1

| CLASS | EXAMPLES |
| --- | --- |
| Antioxidants | Alpha-tocopherol, lazaroid, probucol, phenolic antioxidant, resveretrol, AGI-1067, vitamin E |
| Antihypertensive Agents | Diltiazem, nifedipine, verapamil |
| Antiinflammatory Agents | Glucocorticoids (e.g. dexamethazone, methylprednisolone), leflunomide, NSAIDS, ibuprofen, acetaminophen, hydrocortizone acetate, hydrocortizone sodium phosphate, macrophage-targeted bisphosphonates |
| Growth Factor Antagonists | Angiopeptin, trapidil, suramin |
| Antiplatelet Agents | Aspirin, dipyridamole, ticlopidine, clopidogrel, GP IIb/IIIa inhibitors, abcximab |
| Anticoagulant Agents | Bivalirudin, heparin (low molecular weight and unfractionated), wafarin, hirudin, enoxaparin, citrate |
| Thrombolytic Agents | Alteplase, reteplase, streptase, urokinase, TPA, citrate |
| Drugs to Alter Lipid Metabolism (e.g. statins) | Fluvastatin, colestipol, lovastatin, atorvastatin, amlopidine |
| ACE Inhibitors | Elanapril, fosinopril, cilazapril |
| Antihypertensive Agents | Prazosin, doxazosin |
| Antiproliferatives and Antineoplastics | Cyclosporine, cochicine, mitomycin C, sirolimus micophenonolic acid, rapamycin, everolimus, tacrolimus, paclitaxel, QP-2, actinomycin, estradiols, dexamethasone, methatrexate, cilostazol, prednisone, cyclosporine, doxorubicin, ranpirnas, troglitzon, valsarten, pemirolast, C-MYC antisense, angiopeptin, vincristine, PCNA ribozyme, 2-chloro-deoxyadenosine |
| Tissue growth stimulants | Bone morphogeneic protein, fibroblast growth factor |
| Promotion of hollow organ occlusion or thrombosis | Alcohol, surgical sealant polymers, polyvinyl particles, 2-octyl cyano-acrylate, hydrogels, collagen, liposomes |
| Functional Protein/Factor delivery | Insulin, human growth hormone, estradiols, nitric oxide, endothelial progenitor cell antibodies |
| Second messenger targeting | Protein kinase inhibitors |
| Angiogenic | Angiopoetin, VEGF |
| Anti-Angiogenic | Endostatin |
| Inhibition of Protein Synthesis/ECM formation | Halofuginone, prolyl hydroxylase inhibitors, C-proteinase inhibitors |
| Antiinfective Agents | Penicillin, gentamycin, adriamycin, cefazolin, amikacin, ceftazidime, tobramycin, levofloxacin, silver, copper, hydroxyapatite, vancomycin, ciprofloxacin, rifampin, mupirocin, RIP, kanamycin, brominated furonone, algae byproducts, bacitracin, oxacillin, nafcillin, floxacillin, clindamycin, cephradin, neomycin, methicillin, oxytetracycline hydrochloride, Selenium. |
| Gene Delivery | Genes for nitric oxide synthase, human growth hormone, antisense oligonucleotides |
| Local Tissue perfusion | Alcohol, H2O, saline, fish oils, vegetable oils, liposomes |
| Nitric oxide Donor Derivatives | NCX 4016 - nitric oxide donor derivative of aspirin, SNAP |
| Gases | Nitric oxide, compound solutions |
| Imaging Agents | Halogenated xanthenes, diatrizoate meglumine, diatrizoate sodium |
| Anesthetic Agents | Lidocaine, benzocaine |
| Descaling Agents | Nitric acid, acetic acid, hypochlorite |
| Anti-Fibrotic Agents | Interferon gamma - 1b, Interluekin - 10 |
| Immunosuppressive/ Immunomodulatory Agents | Cyclosporine, rapamycin, mycophenolate motefil, leflunomide, tacrolimus, tranilast, interferon gamma-1b, mizoribine |
| Chemotherapeutic Agents | Doxorubicin, paclitaxel, tacrolimus, sirolimus, fludarabine, ranpirnase |
| Tissue Absorption Enhancers | Fish oil, squid oil, omega 3 fatty acids, vegetable oils, lipophilic and hydrophilic solutions suitable for enhancing medication tissue absorption, distribution and permeation |
| Anti-Adhesion Agents | Hyaluronic acid, human plasma derived surgical sealants, and agents comprised of hyaluronate and carboxymethyl-cellulose that are combined with dimethylaminopropyl, ehtylcarbodimide, hydrochloride, PLA, PLGA |
| Ribonucleases | Ranpirnase |
| Germicides | Betadine, iodine, sliver nitrate, furan derivatives, nitrofurazone, benzalkonium chloride, benzoic acid, salicylic acid, hypochlorites, peroxides, thiosulfates, salicylanilide |
| Antiseptics | Selenium |
| Analgesics | Bupivicaine, naproxen, ibuprofen, acetylsalicylic acid |

Some specific examples of therapeutic agents useful in the anti-restenosis realm include cerivastatin, cilostazol, fluvastatin, lovastatin, paclitaxel, pravastatin, rapamycin, a rapamycin carbohydrate derivative (for example, as described in US Patent Application Publication 2004/0235762), a rapamycin derivative (for example, as described in U.S. Pat. No. 6,200,985), everolimus, seco-rapamycin, seco-everolimus, and simvastatin. With systemic administration, the therapeutic agent is administered orally or intravenously to be systemically processed by the patient. However, there are drawbacks to a systemic delivery of a therapeutic agent, one of which is that the therapeutic agent travels to all portions of the patient's body and can have undesired effects at areas not targeted for treatment by the therapeutic agent. Furthermore, large doses of the therapeutic agent only amplify the undesired effects at non-target areas. As a result, the amount of therapeutic agent that results in application to a specific targeted location in a patient may have to be reduced when administered systemically to reduce complications from toxicity resulting from a higher dosage of the therapeutic agent.

Accordingly, an alternative to the systemic administration of a therapeutic agent is the use of a targeted local therapeutic agent delivery approach. With local delivery of a therapeutic agent, the therapeutic agent is administered using a medical device or apparatus, directly by hand, or sprayed on the tissue, at a selected targeted tissue location of the patient that requires treatment. The therapeutic agent emits, or is otherwise delivered, from the medical device apparatus, and/or carrier, and is applied to the targeted tissue location. The local delivery of a therapeutic agent enables a more concentrated and higher quantity of therapeutic agent to be delivered directly at the targeted tissue location, without having broader systemic side effects. With local delivery, the therapeutic agent that escapes the targeted tissue location dilutes as it travels to the remainder of the patient's body, substantially reducing or eliminating systemic side effects.

Targeted local therapeutic agent delivery using a medical device can be further broken into two categories, namely, short term and long term ranging generally within a matter of seconds or minutes to a few days or weeks to a number of months. Typically, to achieve the long term delivery of a therapeutic agent, the therapeutic agent must be combined with a delivery agent, or otherwise formed with a physical impediment as a part of the medical device, to slow the release of the therapeutic agent.

Prior attempts to create films and drug delivery platforms, such as in the field of stents, primarily make use of high molecular weight synthetic polymer based materials to provide the ability to better control the release of the therapeutic agent. Essentially, the polymer in the platform releases the drug or agent at a predetermined rate once implanted at a location within the patient. Regardless of how much of the therapeutic agent would be most beneficial to the damaged tissue, the polymer releases the therapeutic agent based on properties of the polymer. Accordingly, the effect of the therapeutic agent is substantially local at the surface of the tissue making contact with the medical device having the coating. In some instances the effect of the therapeutic agent is further localized to the specific locations of, for example, stent struts or mesh pressed against the tissue location being treated. These prior approaches can create the potential for a localized toxic effect.

The stand-alone film 100 of the present invention, however, makes use of the natural oils to form a non-polymeric natural oil based therapeutic agent delivery platform, if desired. Furthermore, the stand-alone film 100 can be formed in a manner that creates the potential for controlled long term release of a therapeutic agent, while still maintaining the benefits of the natural oil component of the stand-alone film 100.

For drug loading, a therapeutic agent is combined with a fatty acid compound prior to formation of the film in accordance with one embodiment of the present invention. Hence, the resultant film has the therapeutic agent interspersed throughout the film. For drug coating, a therapeutic agent is applied in the form of a coating on a stand-alone film. In one embodiment, a coating can be applied by overlaying a drug-loaded fatty acid compound on a stand-alone film. After a therapeutic agent is dissolved in an appropriate solvent, it is blended with a fatty acid compound to form a coating material. The solvent is evaporated prior to applying the coating material as a coating on a stand-alone film. Alternatively, the therapeutic agent may be blended directly into the fatty acid compound without the use of a solvent. The coating material can be, for example, sprayed or brushed onto a stand-alone film. The coating material can also be cast directly on top of a stand-alone film. The stand-alone film with the coating material is heated or exposed to UV light to raise the viscosity of the coating material beyond the gelation point and hence create a cross-linked gel coating on the stand-alone film. Alternatively, the coating material can be left in a state of lower viscosity to preserve drug recovery rate or to alter the release characteristics of the therapeutic agent used in the coating material.

In accordance with one embodiment of the present invention, a coating can be applied using a polyionic layer-by-layer (LBL) technique. A stand-alone film is contacted by a cationic solution (+ charged) for a period of time, after which the stand-alone film is rinsed with deionized water. This results in the stand-alone film being added with a layer of positively charged polyelectrolyte coating. Another layer of coating is then applied by contacting the stand-alone film with an anionic solution (− charged) for a period of time, after which the stand-alone film is again rinsed with deionized water. One or ordinary skill in the art will appreciate that the concentration of the polyelectrolytes can be varied. A therapeutic agent is coated onto the stand-alone film by substituting the therapeutic agent for one of the polyelectrolyte components of the LBL system. After the therapeutic agent is applied, the stand-alone film may be rinsed with deionized water. Using this general procedure, a single drug layer can be coated on the surface of the stand-alone film. Alternatively, a capping polyelectrolyte bilayer can be applied after the drug is coated onto the surface of the stand-alone film and the procedure can be repeated several times to create multiple buried drug layers.

In accordance with yet another embodiment of the present invention, a coating can be applied by dipping a stand-alone film in a solvent-therapeutic mixture to load the therapeutic agent onto the stand-alone film. A therapeutic agent is dissolved in an appropriate solvent. The stand-alone film is then dipped into the solution for a period of time to coat the surface of the film or to allow the film to swell and absorb some of the solution. The stand-alone film is then removed and the solvent in the film is evaporated. Examples of solvents that may be used with this method include, but are not limited to, ethanol and nMP.

The stand-alone film of the present invention may be used as a barrier to keep tissues separated to avoid adhesion. Application examples for adhesion prevention include abdominal surgeries, spinal repair, orthopedic surgeries, tendon and ligament repairs, gynecological and pelvic surgeries, and nerve repair applications. The stand-alone film may be applied over the trauma site or wrapped around the tissue or organ to limit adhesion formation. The addition of therapeutic agents to the stand-alone films used in these adhesion prevention applications can be utilized for additional beneficial effects, such as pain relief or infection minimization. Other surgical applications of the stand-alone film may include using a stand-alone film as a dura patch, buttressing material, internal wound care (such as a graft anastomotic site), and internal drug delivery system. The stand-alone film may also be used in applications in transdermal, wound healing, and non-surgical fields. The stand-alone film may be used in external wound care, such as a treatment for burns or skin ulcers. The stand-alone film may be used without any therapeutic agent as a clean, non-permeable, non-adhesive, non-inflammatory, anti-inflammatory dressing, or the stand-alone film may be used with one or more therapeutic agents for additional beneficial effects. The stand-alone film may also be used as a transdermal drug delivery patch when the stand-alone film is loaded or coated with one or more therapeutic agents.

The process of wound healing involves tissue repair in response to injury and it encompasses many different biologic processes, including epithelial growth and differentiation, fibrous tissue production and function, angiogenesis, and inflammation. The cross-linked gel used to make the inventive stand-alone film has been shown in an animal model not to produce an inflammatory response, but still provide excellent cellular overgrowth with little to no fibrous capsule formation. Accordingly, the stand-alone film provides an excellent material suitable for wound healing applications.

Figure 6A:
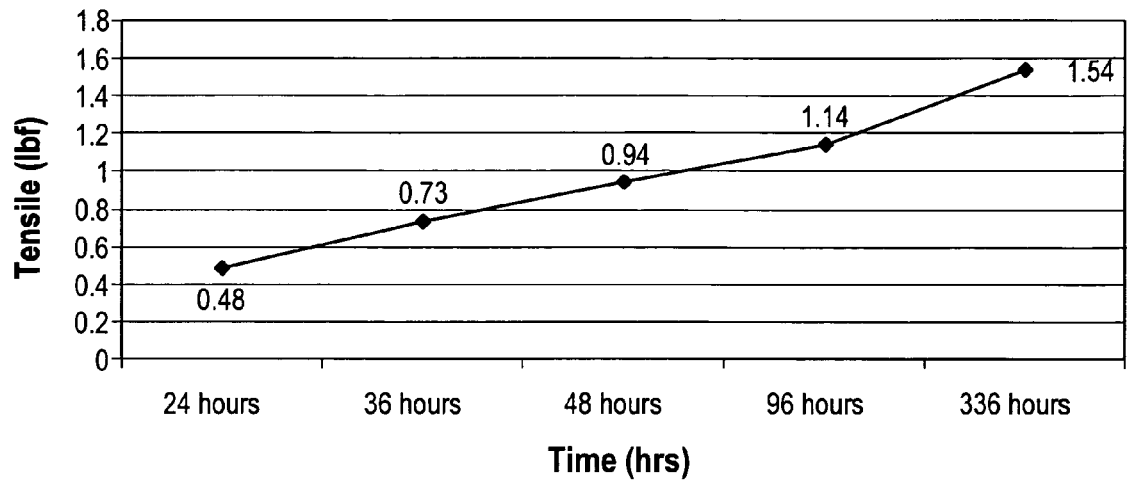
FIG. 6A is a graph showing tensile strength as a function of treatment time when a film was processed at 200° F.
Figure 6B:
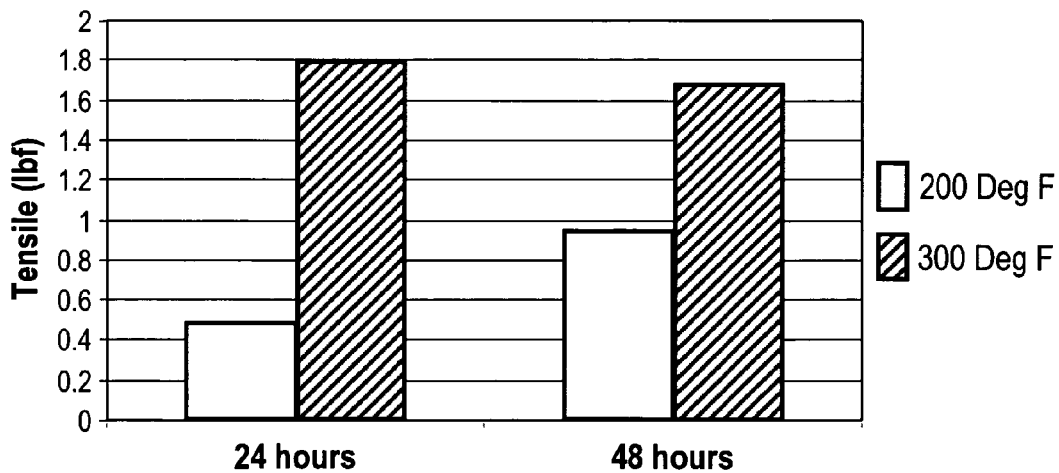
FIG. 6B is a graph showing tensile strength as a function of processing temperature.

In general, the thicker the film, the longer it takes for the film to be absorbed by a patient's body. Furthermore, processing parameters, such as processing time, processing temperature, and processing method, can also influence the breakdown characteristic of a stand-alone film. Additionally, the thicker the film, the stronger the film as measured with tensile strength. Tensile strength varies with processing time and processing temperature. FIG. 6A demonstrates the increase in tensile strength of 5-mil-thick films as a function of processing time at 200° F. All films were cast from pre-thickened fish oil (~15,500 cP @ 24° C.) onto a PTFE mat and placed under UV lamps (15 watts and 254 nm) for 15 minutes. The films were then heated in the oven with a set temperature of 200° F. FIG. 6B illustrates variations in tensile strength as a function of processing temperature. All films were cast from pre-thickened fish oil (~15,500 cP @ 24° C.) onto a PTFE mat and placed under UV lamps (15 watts and 254 nm) for 15 minutes. The films were then heated in an oven with a set temperature of either 200° F. or 300° F. The films were heated for 24 hours and 48 hours and the tensile strength were measured as shown in FIG. 6B. One of ordinary skill in the art will appreciate that many factors can vary film performance, such as the time and temperature of the heating treatment, the time and intensity of the UV treatment, the type of fatty acid compound used, and any therapeutic agent that is added to the film.

The stand-alone film of the present invention has shown improved tensile strength properties compared to Sepraﬁlm® manufactured by Genzyme Corporation. When Sepraﬁlm is dry, the tensile strength is about 13.5 lbf. However, when exposed to normal saline in conditions similar to 30 seconds after implantation, Sepraﬁlm's tensile strength reduces to 0.059 lbf due to hydration. On the other hand, a stand-alone film in accordance with the present invention with a thickness that is about the same as Sepraﬁlm has a tensile strength of 0.48 lbf (when the film was made using the same process as the samples shown in FIG. 6A and the heating time was 24 hours) and the tensile strength does not change after 30 seconds under normal saline conditions. Hence, the stand-alone film can provide improved anti-adhesion protection compared to Sepraﬁlm. Sepraﬁlm is designed to degrade within about 7 days, whereas the stand-alone film of the present invention can be designed to degrade in a period of weeks to months. Hence, the stand-alone film can be used to provide longer anti-adhesion protection where adhesion is likely to occur after 7 days. Furthermore, because Sepraﬁlm loses its tensile strength dramatically when it encounters moisture, it is difficult to handle Sepraﬁlm before and during the process of implantation. However, the tensile strength of a stand-alone film of the present invention does not change with moisture in a short period of time, such as within 30 seconds. Hence, the stand-alone film is substantially easier to handle.

Method of Making Example #1

One example of making a stand-alone film using the methods shown in FIG. 2 with a flat substrate, such as shown in FIG. 3A, was demonstrated using a polytetrafluoroethylene (PTFE) substrate. EPAX 3000 TG fish oil was heated at 200° F. for a week until the viscosity of the fish oil reaches 15,500 cps at 24° C. The thickened fish oil was cast directly onto a mat of PTFE by using a controlled applicator, such as a micrometer controlled film casting knife with a gap setting of 0.0015 inches. The PTFE mat with the thickened fish oil on top was then placed under a UV lamp for 15 minutes. The UV lamp had a power of 15 watts and emitted UV light with a 254 nm wavelength. After exposing the thickened fish oil to UV light, it was then heated in an oven at 200° F. for 24 hours to completely cure the thickened fish oil. The resultant film was removed from the PTFE mat to form a stand-alone film. The film's thickness was measured to be 0.005 inches using a snap gauge. The film was soft, flexible, durable and easy to handle with bare hands or gloves.

Method of Making Example #2

Another example of making a stand-alone film using the method shown in FIG. 2 and a substrate such as those shown in FIGS. 3B and 3C was demonstrated using a Pyrex Petri dish. The Pyrex Petri dish was filled halfway with fish oil and then covered with an ePTFE cover, where the ePTFE material had an internodal distance of between 5 to 20 microns. The Petri dish was turned upside down (ePTFE side down) and placed into an oven. The temperature of the oven was set to 200° F. The Petri dish was left in the oven for 24 hours. After the Petri dish had been in the oven for the desired amount of time, the Petri dish was removed from the oven and kept upside down to allow the fish oil to cool to room temperature. When the fish oil had cooled down, the ePTFE cover was pierced near the edge to allow excess fish oil to drain out. Thus, a semi-cured layer of film was left behind on the ePTFE cover. The Petri dish, along with the ePTFE cover and the semi-cured film were then placed back into the oven for 4 hours to finish the curing process. After the film was completely cured, the Petri dish was removed from the oven and allowed to cool. When the Petri dish was cooled, the ePTFE cover was removed from the dish and the film was peeled away from the ePTFE cover to form a stand-alone film.

Method of Making Example #3

An example of making a stand-alone film using the method shown in FIG. 4 was demonstrated by using an expanded polytetrafluoroethylene (ePTFE) tube that has an internal diameter of 24 millimeters. The ePTFE material has an internodal distance of between 5 to 20 microns. EPAX® fish oil from Pronova Biocare was used to fill the ePTFE tube. The filled ePTFE tube was then placed in the oven for 48 hours at 200° F. The heated ePTFE tube was then removed from the oven and any excess fish oil was drained. A thin film was left behind on the tube internal wall surface after draining the excess fish oil. The ePTFE tube was cut open lengthwise and the film was peeled from the internal wall of the ePTFE tube to form a stand-alone film.

Drug Loading Example #1

Figure 7:
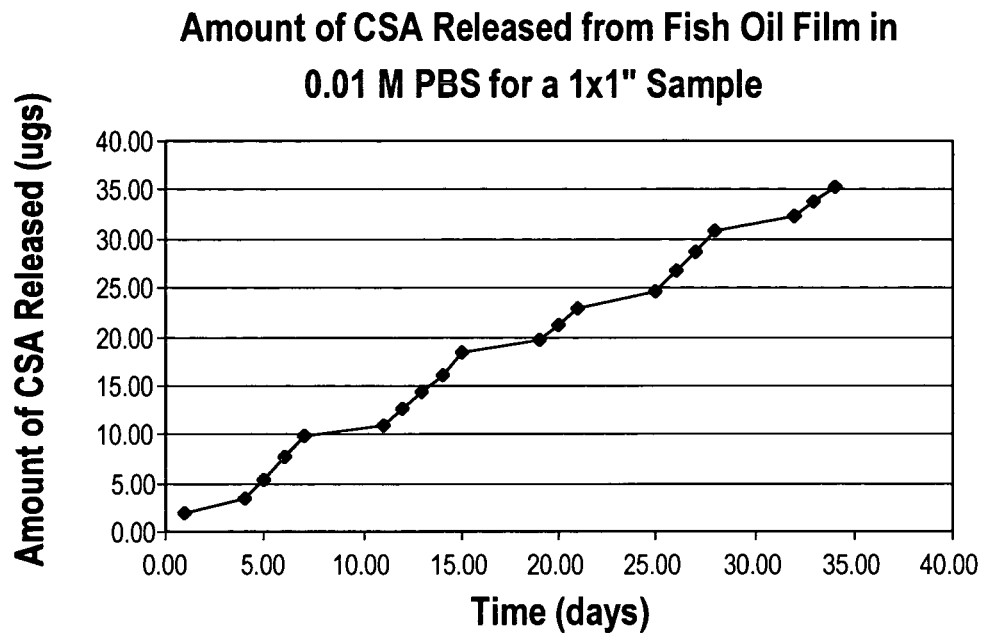
FIG. 7 is a graph showing the amount of a therapeutic agent released from a fish oil film sample as a function of time when the therapeutic agent was loaded into the film.

One example of using drug loading was demonstrated by using Cyclosporine. Pure fish oil was heated at 200° F. to obtain a viscosity of 15,000-20,000 cps at 24° C. to form a pre-treated or pre-thickened fish oil. 3.1 g of the pre-treated or pre-thickened fish oil is then mixed with 64.6 mg of Cyclosporine A (CSA). The mixture was then heated to 150° F. for 20 minutes to allow the CSA to dissolve in the fish oil. This resulted in a 2.0% CSA in fish oil formulation by weight. After heating, the mixture was cast onto a Teflon mat with a casting knife to form a thin film. The thin film was then placed under a UV lamp for 15 minutes. The UV lamp had a power of 15 watts and emitted UV light with a 254 nm wavelength. After exposure to UV light, the thin film was heated in an oven at 200° F. for 24 hours, after which the thin film was removed from the oven and allowed to cool for 1 hour. After the thin film was cooled, it was peeled from the Teflon mat to form a stand-alone film. The resultant film had a thickness of approximately 0.005". Drug extraction and dissolution were performed on the film by high performance liquid chromatography (HPLC). The extraction result shows a CSA load of 311 μg on a 1" by 1" sample. The dissolution results are shown in FIG. 7. In general, the dissolution results showed that CSA was released in an approximately linear fashion as a function of time.

Drug Coating Example #1

Figure 8:
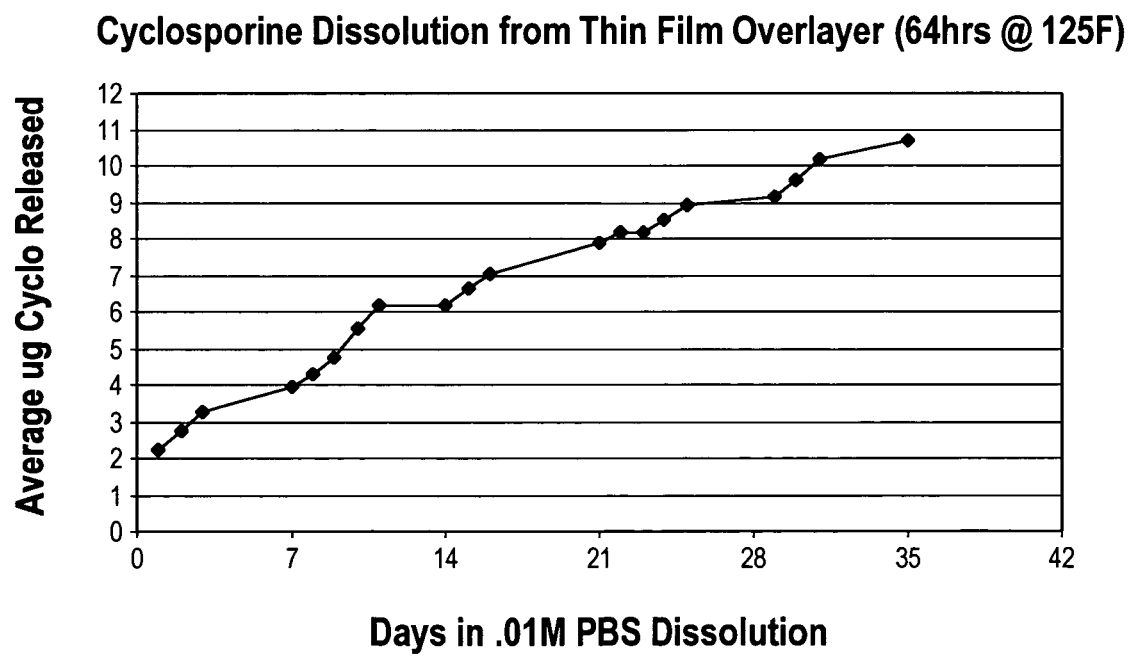
FIG. 8 is a graph showing the amount of a therapeutic agent released from a fish oil film sample as a function of time when the therapeutic agent was coated onto the film using an overlaying method.

An example of using drug coating was demonstrated by overlaying a drug-loaded fish oil on a stand-alone film. Pure fish oil was heated at 200° F. to obtain a viscosity greater than 100,000 cps at 24° C. to form pre-cured fish oil. 3.33 g of pre-cured fish oil was mixed with 71.1 mg of CSA to form a mixture. This resulted in a 2.1% CSA in fish oil formulation by weight. After the CSA was solubilized in the pre-cured fish oil, the mixture was brushed onto a 1" by 1½ piece of stand-alone film. The film with the drug coating was then heated at 125° F. for 64 hours. Drug extraction and dissolution were performed on the film by HPLC. The extraction result shows a CSA load of 3.2 mg on a 1" by 1½" sample. FIG. 8 shows the dissolution results. In general, the dissolution results showed that CSA was released in an approximately linear fashion as a function of time.

Drug Coating Example #2

Another example of drug coating was demonstrated by using the polyionic LBL technique. A coating of Marcaine was added to a piece of stand-alone film by applying a polyelectrolyte coating (LBL) on a 1" by 1½" of stand-alone film. The cationic component was 0.01M polyethylene amine (PEI) while the anionic component was 0.01M poly acrylic acid (PAA). A 10-layer system was added to the stand-alone film beginning with PEI and ending with PAA, with a 5-minute soak for each component followed by a deionized water rinse. 103.2 mg of Marcaine was added to 3.5 ml of water to form a 29.5 mg/ml Marcaine solution. The stand-alone film was then dipped into the Marcaine solution for 5 minutes and allowed to air dry.

Drug Coating Example #3

Figure 9:
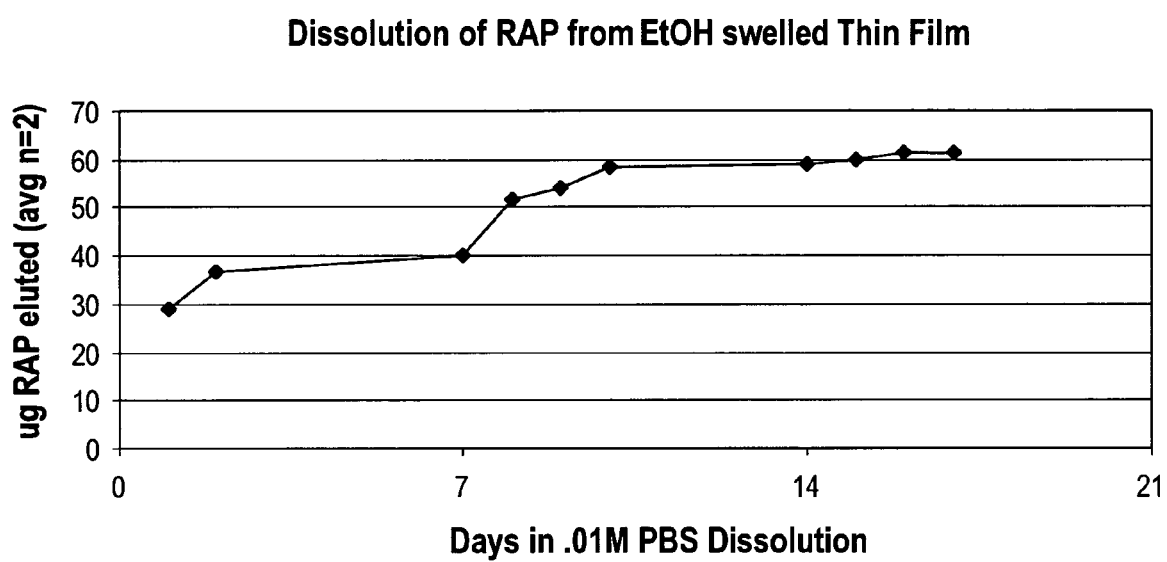
FIG. 9 is a graph showing the amount of a therapeutic agent released from a fish oil film sample as a function of time when the film was dipped into a solution containing the therapeutic agent and allowed to swell.

Still another example of drug coating was demonstrated by allowing a stand-alone film to swell with a solution including a therapeutic agent. 40.1 mg of RAP was mixed with 3.6 g of EtOH. This resulted in a 10% RAP in Ethanol formulation by weight. A 1" by 1½" of stand-alone film was dipped into the RAP formulation and allowed to swell. The stand-alone film was then allowed to air dry. The resultant film was approximately 0.005" in thickness. Drug extraction and dissolution were performed on the film by HPLC. The extraction result shows a RAP load of 4.7 mg on a 1" by 1½" sample. Dissolution results are shown in FIG. 9.

For the development of the present invention, experiments were performed using native fish oil with various substrates, such as metal plates, glass plates, PTFE coated pans, non-porous PTFE, and polyvinyl alcohol (PVA) films. The native fish oil was coated on the various substrates and then heated at a set temperature and time to cure the native fish oil. In this manner, the fish oil cures or sets at the exposed surface (top-down) forming a skin (solidified fish oil) on the surface. It was determined that the amount of fish oil required to form a film is limited due to pooling on the substrate. Additionally, the fish oil does not spread out in an even manner due to surface tension. Therefore, there is a limit on how thin the fish oil may be cast on the substrates using this method. Furthermore, the film may start to wrinkle during the curing process or the fish oil may flow and run off the substrate when the substrate is not perfectly leveled in the oven. The resultant film may be of poor quality or may not be reproduced consistently when certain substrates are used. However, using a porous substrate, such as ePTFE, with liquid fish oil or a non-porous substrate with a pre-thickened fish oil can resolve the above mentioned difficulties. Liquid fish oil penetrates into the porous substrate and thus creates a mechanical lock during the curing process to prevent the film from wrinkling. One of ordinary skill in the art will appreciate that any drying or semi-drying oils may also be used with a porous substrate. Using a pre-thickened fish oil on a non-porous substrate provides a different surface tension between the fish oil and the substrate so that the thickened fish oil may be spread out evenly on the substrate.

The present invention provides methods for making stand-alone films from fatty acids. The bioabsorbable nature of the stand-alone film results in the film being completely absorbed over time by the cells of the body tissue. There is no breakdown of the stand-alone film into components and substances that are inflammatory and are eventually distributed throughout the body and in some instances disposed of by the body, as in the case with biodegradable synthetic polymer surgical films. In addition, the stand-alone film also provides a lubricious or anti-adhesive surface against body tissues. The fatty acid derived cross-linked gel that makes up the stand-alone film maintains anti-inflammatory and/or non-inflammatory properties that helps lower the inflammatory response of the body tissues. The reduced inflammation also reduces adhesions. A stand-alone film made from fatty acid compounds is flexible, easy to handle, and can be shaped easily. A therapeutic agent may be applied to a stand-alone film through drug loading or drug coating. Hence, the stand-alone film not only provides anti-adhesion but also therapeutic healing functions.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the invention, and exclusive use of all modifications that come within the scope of the disclosed invention is reserved.

What is claimed is:

1. A film, comprising: a non-polymeric cross-linked gel material formed at least in part of a fish oil fatty acid, wherein the fish oil fatty acid comprises omega-3 fatty acids, and wherein the film is a stand-alone film in the form of a sheet having a first side, a second side opposite the first side, and a perimeter defining a shape.

2. The stand-alone film of claim 1, wherein the omega-3 fatty acid comprises one or more of eicosapentaenoic acid, docosahexaenoic acid or derivatives, analogs and pharmaceutically acceptable salts thereof.

3. The stand-alone film of claim 1, further comprising a vitamin E.

4. The stand-alone film of claim 3, wherein the vitamin E compound comprises one or more of alpha-tocopherol, beta-tocopherol, delta-tocopherol, gamma-tocopherol, alpha-tocotrienol, beta-tocotrienol, delta-tocotrienol, gamma-tocotrienol, alpha-tocopherol acetate, beta-tocopherol acetate, gamma-tocopherol acetate, delta-tocopherol acetate, alpha-tocotrienol acetate, beta-tocotrienol acetate, delta-tocotrienol acetate, gamma-tocotrienol acetate, alpha-tocopherol succinate, beta-tocopherol succinate, gamma-tocopherol succinate, delta-tocopherol succinate, alpha-tocotrienol succinate, beta tocotrienol succinate, delta-tocotrienol succinate, gamma-tocotrienol succinate, mixed tocopherols, derivatives, analogs and pharmaceutically acceptable salts thereof.

5. The stand-alone film of claim 1, wherein the fish oil fatty acid is cured to increase viscosity to form the film.

6. The stand-alone film of claim 5, wherein the fish oil fatty acid is cured using at least one treatment method selected from a group of treatment methods comprised of application of UV light, application of heat, airflow, and reaction with a gas or chemical cross-linker.

7. The stand-alone film of claim 1, further comprising a therapeutic agent, wherein the therapeutic agent comprises an agent selected from the group consisting of analgesics, anti-oxidants, anti-inflammatory agents, anti-coagulant agents, drugs to alter lipid metabolism, anti-proliferatives, anti-neoplastics, tissue growth stimulants, functional protein/factor delivery agents, anti-infective agents, imaging agents, anesthetic agents, chemotherapeutic agents, tissue absorption enhancers, anti-adhesion agents, germicides, analgesics, pro-drugs, and antiseptics.

8. The stand-alone film of claim 7, wherein the therapeutic agent is combined with the fish oil fatty acid prior to formation of the film, resulting in the therapeutic agent being interspersed throughout the film.

9. The stand-alone film of claim 7, wherein the therapeutic agent is applied to the film in the form of a coating.

10. The stand-alone film of claim 1, wherein the film is bioabsorbable.

11. The stand-alone film of claim 1, wherein the film maintains anti-adhesive properties.

12. A method of forming a stand-alone film, comprising: providing a chamber formed of flexible porous material and having an internal wall; filling the chamber with a fish oil fatty acid compound in liquid form, wherein the fish oil fatty acid compound comprises omega-3 fatty acids; curing the fish oil fatty acid compound proximal to the internal wall to form a film of non-polymeric cross-linked gel material along the internal wall; removing the fish oil fatty acid compound that remains in liquid form; and separating the film from the internal wall of the flexible porous material creating a stand-alone film of non-polymeric cross-linked gel material in the form of a sheet having a first side, a second side opposite the first side, and a perimeter defining a shape.

13. The method of claim 12, wherein the flexible material comprises expanded polytetrafluoroethylene (ePTFE).

14. The method of claim 12, wherein the omega-3 fatty acid comprises one or more of eicosapentaenoic acid, docosahexaenoic acid or derivatives, analogs and pharmaceutically acceptable salts thereof.

15. The method of claim 12, further comprising mixing a vitamin E compound to form a portion of the fish oil fatty acid compound.

16. The method of claim 15, wherein the vitamin E compound comprises one or more of alpha-tocopherol, beta-tocopherol, delta-tocopherol, gamma-tocopherol, alpha-tocotrienol, beta-tocotrienol, delta-tocotrienol, gamma-tocotrienol, alpha-tocopherol acetate, beta-tocopherol acetate, gamma-tocopherol acetate, delta-tocopherol acetate, alpha-tocotrienol acetate, beta-tocotrienol acetate, delta-tocotrienol acetate, gamma-tocotrienol acetate, alpha-tocopherol succinate, beta-tocopherol succinate, gamma-tocopherol succinate, delta-tocopherol succinate, alpha-tocotrienol succinate, beta-tocotrienol succinate, delta-tocotrienol succinate, gamma-tocotrienol succinate, mixed-tocopherols, derivatives, analogs and pharmaceutically acceptable salts thereof.

17. The method of claim 12, wherein curing comprises using at least one treatment method selected from a group of treatment methods comprised of application of UV light, application of heat, airflow, and reaction with a gas or chemical cross-linker.

18. The method of claim 12, further comprising combining a therapeutic agent with the fish oil fatty acid compound.

19. The method of claim 12, further comprising combining a therapeutic agent with the fish oil fatty acid compound prior to formation of the stand-alone film, interspersing the therapeutic agent throughout the stand-alone film.

20. The method of claim 12, further comprising applying a therapeutic agent to the stand-alone film in the form of a coating.

21. A method of forming a stand-alone film, comprising: providing a fish oil fatty acid compound in liquid form, wherein the fish oil fatty acid compound comprises omega-3 fatty acids; applying the fish oil fatty acid compound to a substrate; and curing the fish oil fatty acid compound to form a non-polymeric cross-linked gel material in the form of the stand-alone film having a first side, a second side opposite the first side, and a perimeter defining a shape.

22. The method of claim 21, wherein the substrate comprises expanded polytetrafluoroethylene (ePTFE) or polytetrafluoroethylene (PTFE).

23. The method of claim 22, wherein the omega-3 fatty acid comprises one or more of eicosapentaenoic acid, docosahexaenoic acid or derivatives, analogs and pharmaceutically acceptable salts thereof.

24. The method of claim 21, further comprising mixing a vitamin E compound to form a portion of the fish oil fatty acid compound.

25. The method of claim 24, wherein the vitamin E compound comprises one or more of alpha-tocopherol, beta-tocopherol, delta-tocopherol, gamma-tocopherol, alpha-tocotrienol, beta-tocotrienol, delta-tocotrienol, gamma-tocotrienol, alpha-tocopherol acetate, beta-tocopherol acetate, gamma-tocopherol acetate, delta-tocopherol acetate, alpha-tocotrienol acetate, beta-tocotrienol acetate, delta-tocotrienol acetate, gamma-tocotrienol acetate, alpha-tocopherol succinate, beta-tocopherol succinate, gamma-tocopherol succinate, delta-tocopherol succinate, alpha-tocotrienol succinate, beta-tocotrienol succinate, delta-tocotrienol succinate, gamma-tocotrienol succinate, mixed tocopherols, derivatives, analogs and pharmaceutically acceptable salts thereof.

26. The method of claim 21, wherein curing comprises using at least one treatment method selected from a group of treatment methods comprised of application of UV light, application of heat, airflow, and reaction with a gas or chemical cross-linker.

27. The method of claim 21 further comprising applying UV light to set the fish oil fatty acid compound by forming a skin on the top surface of the fish oil fatty acid compound in liquid form prior to additional curing.

28. The method of claim 21, further comprising combining a therapeutic agent with the fish oil fatty acid compound.

29. The method of claim 21, further comprising combining a therapeutic agent with the fish oil fatty acid compound prior to formation of the stand-alone film, interspersing the therapeutic agent throughout the stand-alone film.

30. The method of claim 21, further comprising applying a therapeutic agent to the stand-alone film in the form of a coating.

31. The method of claim 21, further comprising treating the fish oil fatty acid compound in liquid form prior to application to the substrate to form a pre-thickened fatty acid compound.

32. The method of claim 21, wherein the substrate has an indentation that is used as a mold to shape the stand-alone film.

33. The method of claim 21 further comprising the step of: cutting the film to a desirable shape.

* * * * *